US011682492B2

(12) United States Patent
Shoaran et al.

(10) Patent No.: US 11,682,492 B2
(45) Date of Patent: Jun. 20, 2023

(54) ENERGY-EFFICIENT ON-CHIP CLASSIFIER FOR DETECTING PHYSIOLOGICAL CONDITIONS

(71) Applicant: Cornell University, Ithaca, NY (US)

(72) Inventors: Mahsa Shoaran, Ithaca, NY (US);
Milad Taghavi, Ithaca, NY (US);
Benyamin Haghi, Ithaca, NY (US);
Masoud Farivar, Ithaca, NY (US);
Azita Emami, Ithaca, NY (US)

(73) Assignees: CORNELL UNIVERSITY, Ithaca, NY (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 336 days.

(21) Appl. No.: 16/946,151

(22) Filed: Jun. 8, 2020

(65) Prior Publication Data
US 2020/0388397 A1    Dec. 10, 2020

Related U.S. Application Data

(60) Provisional application No. 62/858,912, filed on Jun. 7, 2019.

(51) Int. Cl.
*G16H 50/20* (2018.01)
*G16H 50/30* (2018.01)
(Continued)

(52) U.S. Cl.
CPC ............. *G16H 50/20* (2018.01); *A61B 5/725* (2013.01); *A61B 5/7264* (2013.01);
(Continued)

(58) Field of Classification Search
CPC ........ G16H 10/00–80/00; G06N 3/00–99/007; A61B 1/00–2576/026
See application file for complete search history.

(56) References Cited

U.S. PATENT DOCUMENTS 6,024,705 A * 2/2000 Schlager .............. A61B 5/7264
600/508
9,904,659 B1 * 2/2018 Stupp ..................... G16B 40/10
(Continued)

FOREIGN PATENT DOCUMENTS

EP         1916767 A1 * 4/2008  ......... H03H 21/0021
WO    WO-9944498 A1 * 9/1999  ............ G06F 19/00

OTHER PUBLICATIONS

Hu et al., "Automated detection of driver fatigue based on EEG signals using gradient boosting decision tree model," Cognitive Neurodynamics (2018) 12:431-440 https://doi.org/10.1007/s11571-018-9485-1. (Year: 2018).*

(Continued)

*Primary Examiner* — Jonathon A. Szumny
(74) *Attorney, Agent, or Firm* — Cozen O'Connor

(57) ABSTRACT

Methods, systems, and devices are disclosed for an efficient hardware architecture to implement gradient boosted trees for detecting biological conditions. For example, a method of detecting a biological condition includes receiving, by a device, a plurality of physiological signals from a plurality of input channels of the device, selecting, based on a trained prediction model, one or more input channels from the plurality of input channels, converting the one or more physiological signals received from the one or more input channels to one or more digital physiological signals, identifying, by using the plurality of gradient boosted decision trees, the selected characteristic in the one or more digital physiological signals, and determining a presence of a physiological condition based on an addition of the output values obtained from the plurality of gradient boosted decision trees.

13 Claims, 27 Drawing Sheets

(51) Int. Cl.

| | |
|---|---|
| *G16H 40/67* | (2018.01) |
| *G06N 20/20* | (2019.01) |
| *G06N 5/04* | (2023.01) |
| *A61B 5/00* | (2006.01) |
| *G06N 5/01* | (2023.01) |
| *A61B 5/11* | (2006.01) |
| *G16H 10/60* | (2018.01) |
| *G16H 50/70* | (2018.01) |

(52) U.S. Cl.
CPC .............. *A61B 5/7275* (2013.01); *G06N 5/01* (2023.01); *G06N 5/04* (2013.01); *G06N 20/20* (2019.01); *G16H 40/67* (2018.01); *G16H 50/30* (2018.01); *A61B 5/1101* (2013.01); *A61B 5/4082* (2013.01); *A61B 5/4094* (2013.01); *G16H 10/60* (2018.01); *G16H 50/70* (2018.01)

(56) References Cited

U.S. PATENT DOCUMENTS

| | | | | |
|---|---|---|---|---|
| 11,033,742 | B2* | 6/2021 | Panken | A61N 1/37235 |
| 2007/0055324 | A1* | 3/2007 | Thompson | G16H 40/63 |
| | | | | 128/903 |
| 2009/0182217 | A1* | 7/2009 | Li | A61B 5/4839 |
| | | | | 73/1.02 |
| 2016/0135706 | A1* | 5/2016 | Sullivan | A61B 5/316 |
| | | | | 600/509 |
| 2018/0093092 | A1* | 4/2018 | Howard | A61N 1/0529 |
| 2018/0102926 | A1* | 4/2018 | Marr | H04L 5/06 |
| 2019/0139275 | A1* | 5/2019 | Hao | G06T 11/008 |
| 2022/0051375 | A1* | 2/2022 | Wang | G06V 10/56 |

OTHER PUBLICATIONS

Birjandtalab et al., "Automated seizure detection using limited-channel EEG and non-linear dimension reduction," Computers in Biology and Medicine 82 (2017) 49-58; http://dx.doi.org/10.1016/j.compbiomed.2017.01.011. (Year: 2017).*

Xu et al., "Channel Selection Based on Phase Measurement in P300-Based Brain-Computer Interface," PLoS ONE 8(4): e60608 (2013). doi:10.1371/journal.pone.0060608 (Year: 2013).*

Shoaran et al., "Hardware-Friendly Seizure Detection with a Boosted Ensemble of Shallow Decision Trees," 2016 38th Annual International Conference of the IEEE Engineering in Medicine and Biology Society (EMBC); DOI: 10.1109/EMBC.2016.7591074. (Year: 2016).*

Zhang et al., "Seizure Prediction using Polynomial SVM Classification," Annu Int Conf IEEE Eng Med Biol Soc. Aug. 2015; 2015: 5748-51. doi: 10.1109/EMBC.2015.7319698. (Year: 2015).*

Truong et al., "Supervised learning in automatic channel selection for epileptic seizure detection," Expert Systems With Applications 86 (2017) 199-207; http://dx.doi.org/10.1016/j.eswa.2017.05.055. (Year: 2017).*

Zhang, Zisheng "Low-Complexity Seizure Prediction From iEEG/sEEG Using Spectral Power and Ratios of Spectral Power" IEE Transaction on Biomedical Circuits and Systems, vol. 10, No. 3, Jun. 2016, p. 693-706.

Yao, Lin et al. "Improved detection of Parkinsonian resting tremor with feature engineering and Kalman filtering" Clinical Neurophysiology 131, Elsevier B.V., Sep. 10, 2019, pp. 274-284.

Shoaran, Mahsa, et al. "Energy-Efficient Classification for Resource-Constrained Biomedical Applications" IEEE Journal On Emerging And Selected Topics In Circuits And Systems, vol. 8, No. 4, Dec. 2018, pp. 693-707.

\* cited by examiner

Input: Original trained tree ensemble $\mathcal{T} = \{\mathcal{T}_1, \ldots, \mathcal{T}_k\}$
Output: Delay-constrained ensemble $\mathcal{T}' = \{\mathcal{T}'_1, \ldots, \mathcal{T}'_k\}$
Data: training set $S = \{(x_i, y_i)\}$
  feature set: $F = \{f_i\}$, each with delay $d_i$
  delay tolerance: $\Delta T$
  set of predecessors of node h: $\pi(h)$
for *all trees $\mathcal{T}_i$ in $\mathcal{T}$* do
  for *each node $h \in \{1, \ldots, |\mathcal{T}_i|\}$* do
    if $\sum_{i \in \pi(h)} d_i > \Delta T$ then
      $\forall f_i \in F$ find feasible $f$ that obtains the best
        $SplitCriterion(f_i, S)$
      Label node $h$ with $f$
      Grow $Subtree(h)$
    end
  end
end

FIG. 4

ENERGY-EFFICIENT ON-CHIP CLASSIFIER FOR DETECTING PHYSIOLOGICAL CONDITIONS

CROSS-REFERENCE TO RELATED APPLICATION

This patent document claims priority to U.S. Provisional Application No. 62/858,912, filed on Jun. 7, 2019, entitled "ENERGY-EFFICIENT ON-CHIP CLASSIFIER," the disclosure of which is hereby incorporated by reference herein in its entirety.

TECHNICAL FIELD

This patent document relates to machine learning technology.

BACKGROUND

Despite major advances in medicine and drug therapy over the past decade, many disorders remain largely undertreated. Where medications are poorly effective, stimulation may offer an alternative treatment. For example, neurostimulation is today a well-established therapy for essential tremor, Parkinson's diseases and epilepsy, and has shown promise in migraine and psychiatric disorders. In particular, closed-loop neuromodulation has recently gained attention, e.g., in the form of responsive neurostimulator (RNS) for epilepsy, and adaptive deep brain stimulation for Parkinson's disease.

SUMMARY

Techniques, systems, and devices are disclosed for an efficient hardware architecture to implement gradient boosted trees in applications that can have stringent power, area, and/or delay constraints, such as in medical devices.

An example method of detecting a biological condition is disclosed. The example method includes receiving, by a device, a plurality of physiological signals from a plurality of input channels of the device; selecting, based on a trained prediction model, one or more input channels from the plurality of input channels, where the trained prediction model indicates the one or more input channels and configurations of a plurality of gradient boosted decision trees for identification of a selected characteristic of one or more physiological signals from the plurality of physiological signals; converting the one or more physiological signals received from the one or more input channels to one or more digital physiological signals; identifying, by using the plurality of gradient boosted decision trees, the selected characteristic in the one or more digital physiological signals, where the identifying the selected characteristic includes providing output values by the plurality of gradient boosted decision trees; and determining a presence of a physiological condition based on an addition of the output values obtained from the plurality of gradient boosted decision trees.

In some embodiments, the plurality of gradient boosted decision trees operate in parallel, the identifying the characteristic is performed within an optimum time that is determined based on a plurality of times associated with the plurality of gradient boosted decision trees, and each of the plurality of times indicate an amount of time associated with obtaining an output value from an associated gradient boosted decision tree. In some embodiments, each gradient boosted decision tree is associated with a programmable finite impulse response (FIR) filter that filters or bypasses a digital physiological signal based on the selected characteristic. In some embodiments, the device includes a memory that stores the plurality of gradient boosted decision trees and coefficient values for the programmable FIR filter for each gradient boosted decision tree, and the coefficient values are based on the selected characteristics.

In some embodiments, the programmable FIR filter includes a first stage that outputs a downsampled physiological signal that is obtained by downsampling the digital physiological signal, the programmable FIR filter includes a second stage that includes a tunable bandpass filter that filters the downsampled physiological signal, and bandwidth related parameters of the tunable bandpass filter are determined based on the selected characteristic. In some embodiments, any one or more of the first stage and the second stage are bypassed based on the selected characteristic. In some embodiments, the selecting the one or more input channels is performed using a multiplexer associated with each of the plurality of gradient boosted decision trees. In some embodiments, the selecting, the converting, the identifying, and the determining is performed for the one or more input channels that are selected without buffering data from the plurality of input channels other than the one or more input channels. In some embodiments, a number of the plurality of gradient boosted decision trees is up to eight, and each gradient boosted decision tree has a maximum pre-determined depth of four.

In yet another exemplary aspect, the above-described methods and methods described in this patent document are embodied in the form of processor-executable code and stored in a non-transitory computer-readable storage medium. The code included in the computer readable storage medium when executed by one or more processors, causes the one or more processors to implement the methods described in this patent document.

In yet another exemplary embodiment, a device that is configured or operable to perform the above-described methods is disclosed.

The above and other aspects and their implementations are described in greater detail in the drawings, the descriptions, and the claims.

BRIEF DESCRIPTION OF THE DRAWINGS

FIG. 4 shows a greedy training algorithm to meet the delay constraint.

FIG. 21A shows F1 score, FIG. 22B shows sensitivity, FIG. 22C shows specificity, FIG. 22D shows latency, and FIG. 22E shows performance for monopolar and bipolar configurations with a 1-s window and half overlap, and the boxplot of the corresponding latency on the right axis.

DETAILED DESCRIPTION

Figure 1:
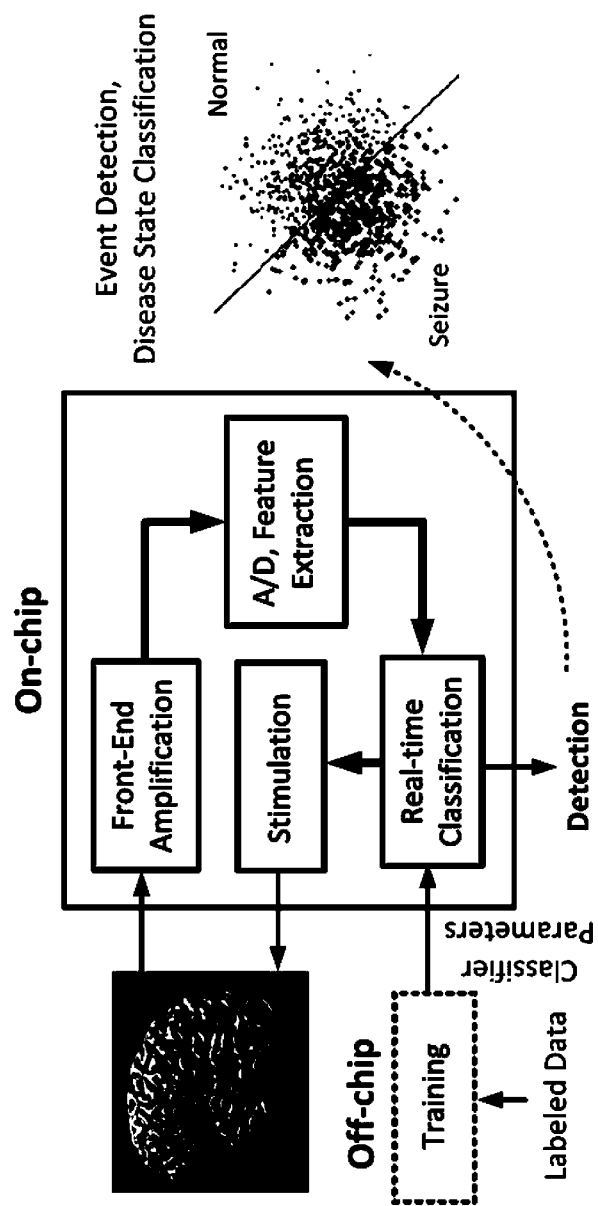
FIG. 1 shows a block diagram of a closed-loop system for detection and suppression of abnormal symptoms in a neurological disease, where an on-chip classifier is embedded into the implantable device.

Medical implants and therapeutic devices often require classifiers that are both accurate and cheap to implement. Deep neural networks achieve the state-of-the-art accuracy in most learning tasks that involve large data sets of unstructured data. However, the application of deep learning techniques may not be beneficial in problems with limited training sets and computational resources, or under domain-specific test time constraints. Among other algorithms, ensembles of decision trees, particularly the gradient boosted models have recently been very successful in machine learning competitions. This patent document describes at least an efficient hardware architecture to implement gradient boosted trees in applications that can have stringent power, area, and/or delay constraints, such as in medical devices. In some embodiments, techniques such as asynchronous tree operation and sequential feature extraction are described to improve energy and/or area efficiency. The proposed classifier can be fabricated in a 65-nm semiconductor process and can consume 41.2 nJ/class. The exemplary classifier design can improve the state-of-the-art by 27 times reduction in energy-area-latency product. The exemplary classifier can also be patient-specific and scalable, which beneficially enables a low-power sensor data classification in biomedical applications.

The example headings for the various sections below are used to facilitate the understanding of the disclosed subject matter and do not limit the scope of the claimed subject matter in any way. Accordingly, one or more features of one example section can be combined with one or more features of another example section.

I. INTRODUCTION

The application of machine learning (ML) techniques has been exponentially growing over the past decade, with an increasing shift toward mobile, wearable and implantable devices. ASIC implementation of machine learning models is required to ensure a sufficiently fast response in real-time applications such as deep brain stimulation and vital sign monitoring. Embedded learning at the edge and near the sensors is also critical in applications with limited communication bandwidth or privacy concerns. Furthermore, to meet the power budget in portable or implantable devices, it is advantageous to embed ML into integrated circuits rather than power-hungry FPGA-based microprocessors.

Deep neural networks (DNNs) currently achieve state-of-the-art accuracy in most learning tasks that involve very large datasets of unstructured data (e.g., vision, audio, natural language processing). As a result, there have been significant research and development efforts to design DNN accelerators and specialized ASICs, like Google's tensor processing units (TPUs). In the context of hardware-friendly machine learning, a number of methods have been recently explored, such as reducing the bit-width precision, sparsity-induced compression, pruning and quantization, and mixedsignal MAC implementation. The focus of these methods is on reducing computation, data movement, and storage in neural networks.

However, application of deep learning techniques may not be practical in problems with limited computational resources, or under application-specific prediction time constraints. For instance, a common requirement of diagnostic devices is to minimize power consumption (down to microwatt-range) and battery usage, while maintaining the desired prediction accuracy and low latency. Moreover, without specialized optimization, straight-forward implementation of conventional classification techniques can be computationally intensive, requiring high processing power and large sizes of memory. Indeed, even the simple arithmetic operations performed in conventional classification methods, such as support vector machine (SVM) and k-nearest neighbor (k-NN) algorithms can become very costly with increasing number of sensors, e.g., in multichannel neural implants. Therefore, there is a need to explore alternative methods for severely resource-constrained applications.

Among other algorithms, Gradient Boosted machines, particularly the XGBoost (XGB) implementation has recently been a winning solution in ML competitions (e.g., the intracranial EEG-based seizure detection contest). This patent document describes an optimization of ensembles of decision tree classifiers and related circuit level architectures for learning applications under stringent power, area, and delay constraints, such as implantable devices. One of the applications of the exemplary embedded classifiers includes closed-loop neuromodulation devices: automatic seizure detection and control in medication-resistant epilepsy. The classifier designs described in this patent document can be used in other types of medical devices for several other diseases and similar application domains.

With the end of Moore's Law, it is foreseeable that energy-quality (EQ) scalable systems will enable power savings that were previously provided by technology and voltage scaling. EQ scaling may, in some cases, break the traditional VLSI design tradeoffs by simultaneously improving the performance, energy and area. In this patent document, hardware-inspired techniques are leveraged to implement decision tree-based classification algorithms, allowing various tree parameters to be employed as tuning knobs for accuracy, latency, and energy optimization. The resulting classifier significantly improves the power and area efficiency of conventional methods, while achieving a higher classification accuracy and sufficient latency, therefore breaking the strict energy-accuracy tradeoff. The tuning parameters include the number and depth of the trees, number of extracted features, window size, and decision update rate. By sophisticated feature engineering and introducing an asynchronous learning scheme, a new class of scalable and low-complexity machine learning hardware for portable sensor-based applications is described in this patent document. Specifically, the energy and quality scalability of the disclosed classifier is analyzed in terms of hardware-related parameters and diagnostic performance.

In this patent document, Sections I to VII describes techniques for a XGB classifier used for seizure detection and Section VIII describes using XGB classifier for detecting Parkinsonian resting tremor. Section II presents a review of current methods that have been used for classification in biomedical domain, and describes their hardware cost and scalability challenges. The exemplary hardware-friendly design of XGB classifier and performance evaluation are presented in Section III and Section IV, respectively. The details of a system on a chip (SoC) implementation and measurement results are presented in Section V followed by a discussion on scalability and hardware optimization in Section VI. Section VII concludes the first part of this patent document. Section VIII describes an improved detection of Parkinsonian resting tremor with feature engineering and Kalman filtering.

II. EMBEDDED CLASSIFICATION IN BIOMEDICAL DEVICES

Despite major advances in medicine and drug therapy over the past decade, many disorders remain largely undertreated. Where medications are poorly effective, stimulation may offer an alternative treatment. For example, neurostimulation is today a well-established therapy for essential tremor, Parkinson's diseases and epilepsy, and has shown promise in migraine and psychiatric disorders. In particular, closed-loop neuromodulation has recently gained attention, e.g., in the form of responsive neurostimulator (RNS) for epilepsy, and adaptive deep brain stimulation for Parkinson's disease.

FIG. 1 shows a block diagram of a closed-loop neural interface system. Following signal conditioning and feature extraction, an embedded classifier detects the disease-associated abnormalities in real time and triggers a programmable stimulator to suppress symptoms of the disease, e.g., a seizure or tremor, through periodic charge delivery to neurons. A high sensitivity, sufficient specificity, and low detection latency are the key requirements for the on-chip classifier, while maintaining a small footprint and low power.

Epilepsy has been a target of neuro-engineering research, along with movement disorders, stroke, and paralysis. Abrupt changes in EEG biomarkers usually precede the clinical onset of seizures. Therefore, ongoing research has been focusing on extracting epileptic biomarkers for automated seizure detection, and closed-loop control through neuromodulation.

Various characteristic features can be extracted from neural data to detect the onset of a particular disease state. A major drawback of conventional classification methods, with the exception of decision trees, is that they must extract all required features from every input channel to classify the data. Therefore, they require extensive computational resources. Filter banks that are commonly used for spectral power extraction in non-overlapping bands are important to diagnose neurological disorders and many other signal classification problems, e.g., voice detection, sleep-state classification, irregular heartbeat detection.

III. HARDWARE-FRIENDLY EXTREME GRADIENT BOOSTING (XGB) CLASSIFIER DESIGN

Figure 2:
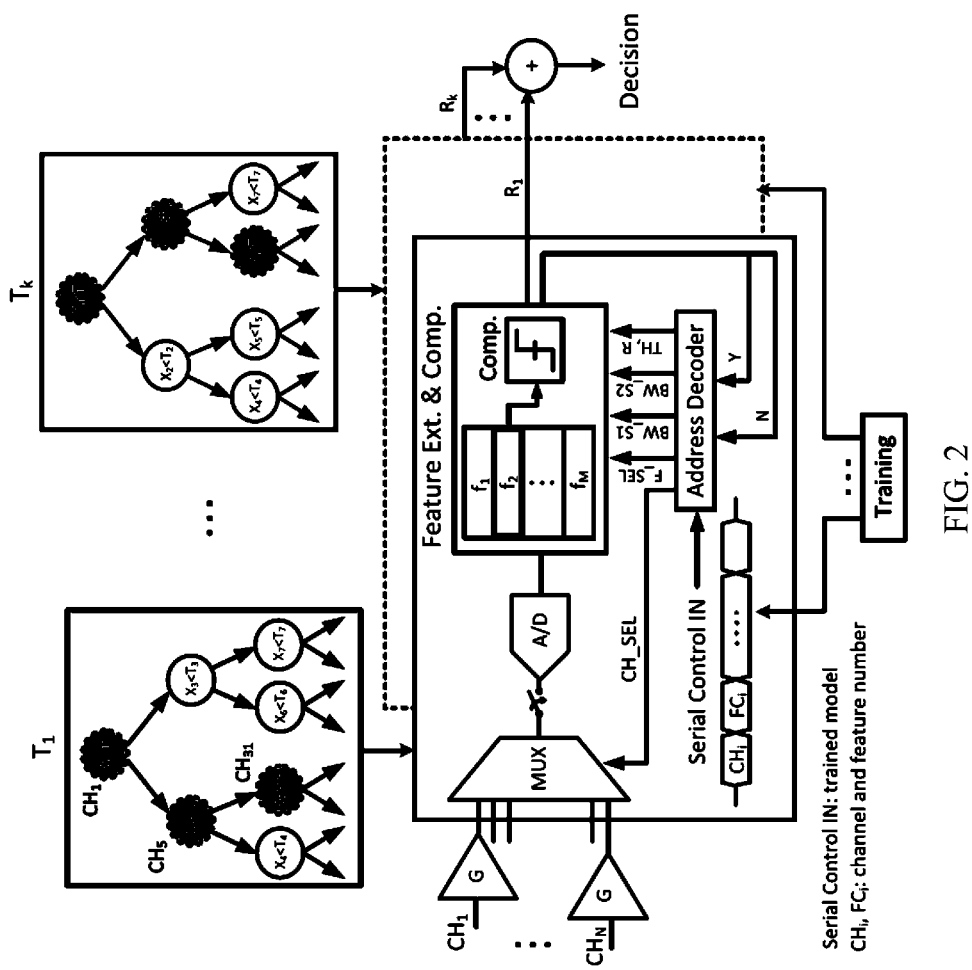
FIG. 2 shows an exemplary hardware architecture for an ensemble of gradient boosted decision trees.

FIG. 2 shows an exemplary hardware-efficient classification algorithm using an ensemble of (or a number of) gradient-boosted decision trees. During a classification task by a decision tree, only one path from the root to the leaf is visited. Therefore, unlike other classifiers, only a limited number of features are necessary in practice to make a decision. These features, however, can be selected by employing powerful training algorithms that produce the optimal tree structure to maximize the overall predictive accuracy. The trained prediction model, which is the output from the gradient-boosting algorithm, includes full information on tree structures in the ensemble such as thresholds, leaf values, and selected features (shown as Serial Control IN in FIG. 2, where CHi and FCi represent the channel number in the array and feature number, respectively). The feature describes a characteristic of a physiological signal that a feature extraction module (as explained below) is expected to extract, where the physiological signal is received by the feature extraction module from a selected channel number.

The hardware architecture is based on at least the following technical features. Since the decision of each tree is made upon completing a series of successive comparisons, a single feature extraction module (shown as Feature Ext. & Comp. in FIG. 2 and also shown as 1330 in FIG. 13) and the preceding ADC (also shown as 1325 in FIG. 13) can be sequentially used to exclusively calculate the requested feature at the current node of a tree. The split direction and next active node of the tree are determined by comparing this requested feature with the corresponding threshold, using, for example a comparator. Therefore, at each step, only the selected channel is used for online feature extraction by the feature extraction module, without buffering the data from other channels or extracting unnecessary features. As shown in FIG. 2, the final answer obtained from the feature extraction module is the sum of answers of all trees as further described in this patent document.

In the exemplary architecture of FIG. 2, a number of (or an ensemble of) up to (and including) eight gradient-boosted decision trees (shown as $T_1$ to $T_k$), each with a programmable feature extraction module (also known as Feature Extraction Engine (FEE)) that includes finite impulse response (FIR) filters (shown as 1335 in FIG. 13) that continuously process a selected input channel(s). The FIR filter can be embedded in the feature extraction engine ($f_1$, $f_2$, ..., $f_M$). In a closed-loop architecture, the FEE reuses a single filter structure to execute the top-down flow of the decision tree, where FIR filter coefficients are multiplexed from a shared memory. This approach results in significant hardware saving. A potential drawback of this serial processing approach would be the degraded latency, that is carefully studied in this Section. The FEE is programmed by a training algorithm (shown on the bottom of FIG. 2) that inputs the control information (e.g., the Serial Control IN shown in FIG. 2), where the control information includes CHi and FCi. In FIG. 2, F_Sel indicates a selected feature number, BW_S1 and BW_S2 indicate a lower frequency value and an upper frequency value for the programmable bandwidth of the filter, and TH,R indicate a threshold value of a requested feature and a result (e.g., leaf value as further described in equation (4) below) of a completed tree.

The proposed architecture enables a low number of FEEs and classification hardware, and therefore, a low complexity. For example, for the proposed hardware architecture, the number of FEE, the number of comparators and the number of Mux can all be one (1) for each gradient-boosted decision tree. The number of FEE modules (or number of computed features) linearly increase with number of channels in conventional technology. Although the exemplary architecture reduces the number of feature extraction and classification (e.g., comparator and multiplexer) units, the memory needed to store the tree structure and FIR filter coefficient values can remain the same as in other tree architectures. The detailed memory breakdown of the exemplary proposed hardware is further discussed in this patent document.

A. Gradient Boosted Trees

Gradient-boosting is one of the most successful machine learning techniques that exploits gradient-based optimization and boosting, by adaptively combining many simple models to get an improved predictive performance. Binary split DTs are commonly used as the "weak" learners. Boosted trees are at the core of state-of-the-art solutions in a variety of learning domains, given their excellent accuracy and fast operation. For example, among the 29 challenge winning solutions published on Kaggle in 2015, 17 used XGB, where DNN was the second most popular method, used in 11 solutions.

Figure 3:
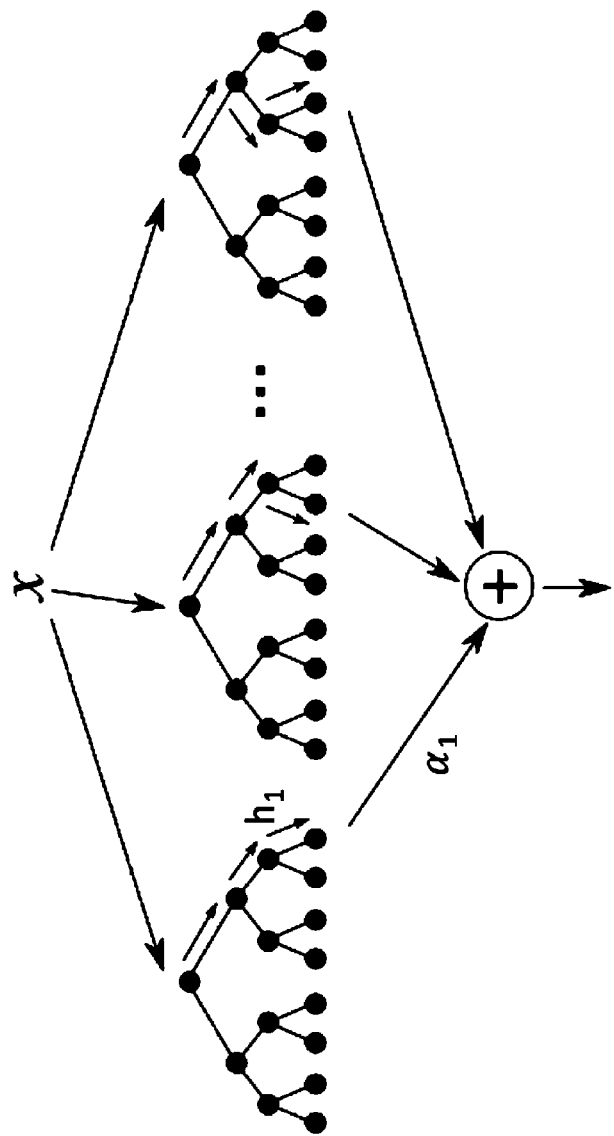
FIG. 3 shows a schematic diagram of a boosted ensemble of decision trees.

Boosting involves creating a number of hypotheses $h_t(x)$ and combining them to form a more accurate composite hypothesis. The output of a boosted classifier (or regressor) with an input feature vector of x has the additive form of $$H(x) = \sum_t \alpha_t h_t(x). \tag{1}$$

where $\alpha_t$ indicates the extent of weight that should be given to $h_t(x)$. A general schematic diagram illustrating an ensemble of depth-3 trees is shown in FIG. 3. FIG. 3 shows three trees, where each tree has a depth of 3 which can allow for 8 leaf nodes or 8 terminal nodes. A number of leaf nodes for a tree can be determined by (2^depth of the tree). Using gradient-boosting, the trees are built in a greedy fashion to minimize a regularized objective on the training loss.

In this patent document, the XGBoost package is employed, a parallelized implementation of the gradient boosting algorithm. To assess the performance of proposed classifier on a relatively large dataset, epilepsy is chosen as a case study, given the availability of continuous recordings from many patients. This architecture, however, can potentially benefit many other on-chip sensor signal classification problems. Applying XGB to the iEEG dataset, over 100 times improvement was observed in training speed compared to common SVM implementations.

In the proposed hardware as shown in FIG. 2, only one channel can be used at each feature computation step in a tree so that the rest of input channels can be switched off to save power. For example, to classify a 100-channel neural data with 8 trees, only 8 channels can be simultaneously active. In contrast to SVM and other methods that require all features from the entire array, this approach significantly reduces the memory and hardware overhead. To reduce energy, a minimum number of trees that obtain a sufficient accuracy are used, that is chosen upon training. Moreover, as a significant advantage, only one tunable bandpass filter can be used to extract as many band-power features as needed, since these features are not computed in parallel. By employing a programmable FIR (or tunable analog) filter, the corresponding FIR filter coefficients (or band selection parameters such as BW_S1 and BW_S2) can be easily multiplexed from memory, according to the feature being processed, as shown in FIG. 2. Besides, as shown later in this patent document, the performance improvement is achieved by using trees with a depth of 4 and above can be very low. Therefore, these ensembles can be made by a relatively small number of low-depth trees (e.g., less than or equal to depth of 4), resulting in significantly lower computational complexity than conventional models.

B. Delay Constraint

The proposed architecture faces a practical challenge of designing decision trees under application-specific delay constraints. Given any ensemble $T=\{T_1, \ldots, T_k\}$ of decision trees obtained from an original method, each tree Ti should satisfy the delay constraint:

$$\sum_{i \in \pi(h)} d_i \le \Delta T \qquad (2)$$

where $d_i$ is the time required to compute feature $f_i$, $\Delta T$ is the maximum tolerable detection delay, and $\pi(h)$ is the set of all predecessors of node h. One possibility is using a "greedy" algorithm to solve this practical constraint by building trees that satisfy the delay requirement, as depicted in FIG. 4. However, this algorithm may result in a suboptimal solution, since the split criterion and subsequent feature selection is subject to the hard constraint on delay.

C. Asynchronous Tree Operation

To solve this issue, an asynchronous approach is introduced where trees freely run in parallel, each with features that maximize the accuracy, regardless of their computational delay. Using the averaged results of completed trees and previous results of incomplete trees, decisions are frequently updated to avoid long latencies.

1) Decision-Making Procedure: First, an optimum time is selected to update the decision of the system. Suppose that k trees are represented by $T_i$, $i \in \{1, 2, \ldots, k\}$. Assuming that $t_i$ is the total time associated with the longest path in $T_i$, the optimum update time is selected as:

$$t_{opt} = \min\{t_1, t_2, \ldots, t_k\} \qquad (3)$$

This guarantees that at least one tree will be completed in this interval, and a new decision is made every $t_{opt}$. Then, the average value of decisions for each tree is calculated as:

$$D_{T_i} = \frac{1}{N_i} \sum_{j=1}^{N_j} r_j \qquad (4)$$

where $N_i$ is the number of completed cycles over $t_{opt}$ and r1, r2, ..., $r_{Ni}$ are the corresponding results (e.g., leaf values) of $T_i$. In a boosting classifier, the answers of all trees must be summed up to make the final decision. Positive answers are classified as seizure detection and negative ones as non-seizure detection. The final result of the system is therefore updated as below:

$$D_{final} = \sum_{i=1}^{k} D_{T_i} \qquad (5)$$

In case there is no new answer for tree $T_i$ after $t_{opt}$, its previous decision is used. By employing this approach and assuming an initial setup time, there always happens to be at least one result produced during $t_{opt}$ to make a decision.

In the proposed asynchronous architecture, each tree continues to test the input data, without waiting for other trees to complete. Suppose that x is a test input that moves through the tree. As x enters node i, it takes time $d_i$ to calculate the feature $f_i$. Based on the value of $f_i$, a split to either right or left branch is made, and the process continues until a leaf is reached. By effectively averaging the decisions of fast trees over multiple cycles, while allowing the longer trees to complete, the overall performance of this online asynchronous approach is even superior to the conventional offline method, where features at different nodes are simultaneously extracted over the same window and decisions are made at the end of this window (a hardware-intensive solution). Since it is likely that more than one answer would be provided by $t_{opt}$, averaging can reduce the impact of noisy decisions. Moreover, features are extracted from successive parts of the decision window, rather than one feature for the entire window. Therefore, the decisions are more accurate, while the optimum selection of update time in (3) reduces the detection latency.

IV. PERFORMANCE EVALUATION

As a benchmark, a boosted ensemble of 8 trees with a maximum depth of 4 using proposed model (XGB-HW) is considered and compared to the linear, cubic, and RBF SVM, k-NN with 3 and 5 neighbors, Logistic Regression, conventional XGB (abbreviated as XGB), Random Forest and Extra Tree classifiers, both configured with 8 trees and a maximum pre-determined depth of 4. A hyperparameter tuning of classifier parameters was performed to find optimum settings.

A. Train/Test Split

Figure 5:
FIG. 5 shows a proposed block-wise data partitioning, where SZ and NSZ represent the seizure and non-seizure segments, respectively.

A common problem in performance evaluation of real-time classifiers such as seizure detectors is to randomly partition the entire data into train and test samples. Shuffling provides prior information from parts of test data (that should remain unseen) during training, resulting in data leakage. A block-wise splitting approach is used to avoid this problem and fairly assess the performance of the exemplary classifier for practical test conditions such as seizure detection. In the block-wise method shown in FIG. 5, the continuous iEEG data is divided into seizure and non-seizure segments, where each seizure is concatenated with the following non-seizure segment into a larger "block" (the first non-seizure segment is added to the beginning of first block). Thus, each block is comprised of a complete seizure attached to the following non-seizure segment. Most patients in the dataset have sufficient and long enough seizure data to allow this approach. However, cases with small number of short seizures are not good candidates for block-wise selection. Therefore, two patients were removed from the initial dataset.

For the purpose of feature extraction during training and offline testing, the time series is divided into 1-s windows and all features from channels are extracted for each window. Block-wise method is compared with the commonly used random split, in which a 5-fold cross-validation is applied to the shuffled data, followed by a hyperparameter tuning to maximize the F1 score for all classifiers. To tune the parameters for the block-wise approach, a block-wise 5-fold cross validation is applied. In this case, 20% of blocks (rounded up to the nearest integer) are retained for testing the model, and the remaining are used as training set. The cross-validation process is then repeated for 5 times and the results are averaged to produce a single estimation. For patients with less than 5 seizures, a block-wise leave-one-out approach was selected, where one block is used as test and the remaining blocks as train, and repeat this for all blocks. To evaluate the corresponding F1 score, sensitivity, and specificity, the tuned parameters for each patient were used and the cross validation results were averaged as described above. For XGB-HW, the trained prediction model generated by the gradient-boosting algorithm includes all the information on tree structures such as leaf values, thresholds and selected features. Using this trained model, the online XGB (XGB-HW) classifier is tested according to the procedure described in Section III.C. To minimize the update interval and latency, features are extracted over smaller time windows than 1 s.

B. Feature Extraction

Based on the initial study on discriminative performance of several frequency and time domain features, and the existing literature, the following set of features were chosen: line-length, total power, time-domain variance, and power in multiple frequency bands, as listed in Table I.

TABLE I

Evaluated Features

| Feature | Description |
| --- | --- |
| Line-Length (LLN) | $\frac{1}{d}\sum_d |x[n] - x[n-1]|$, d = window length |
| Power (POW) | Total spectral power |
| Variance (VAR) | $\frac{1}{d}\sum_d (x[n] - \mu)^2$ where $\mu = \frac{1}{d}\sum_d (x[n])$ |
| Delta ($\delta$) | Spectral power in 1-4 Hz |
| Theta ($\theta$) | Spectral power in 4-8 Hz |
| Alpha ($\alpha$) | Spectral power in 8-13 Hz |
| Beta ($\beta$) | Spectral power in 13-30 Hz |
| Low-Gamma ($\gamma_1$) | Spectral power in 30-50 Hz |
| Gamma ($\gamma_2$) | Spectral power in 50-80 Hz |
| High-Gamma ($\gamma_3$) | Spectral power in 80-150 Hz |
| Ripple | Spectral power in 150-250 Hz |
| Fast Ripple (FR) | Spectral power in 250-600 Hz (@ SR = 5 kHz) |

The discriminative performance of this feature set is analyzed on an extensive iEEG database, in which line-length was the best discriminative feature. While the optimal frequency range was patient-dependent, in majority of patients sampled at a sufficiently high rate (5 k), it had a clear shift from low-frequency bands toward gamma, ripple, and fast ripples. Rather than using the absolute value of spectral power, normalized features were calculated by dividing the spectral power within each frequency band by the total power.

The power values (and corresponding thresholds) typically change with the daily life status of a patient, such as sleep state, physical or mental activities, and consciousness level. In contrast, normalized values are more robust with respect to fluctuations in a patient's daily life and have been utilized in the study. Features are obtained from each iEEG channel using is windows for training and offline testing. During online testing, a minimum extraction time is assigned to each feature, based on their computational delay. Using normalized band powers, an improved seizure detection accuracy is observed compared to absolute spectral power features.

It should be noted that various other features may be included to enable more accurate seizure detection. However, one of the focus of this patent document is on the classification algorithm. The literature pertaining to analysis of various features for epilepsy diagnosis is immense.

C. Depth and Number of Trees

Figure 6:
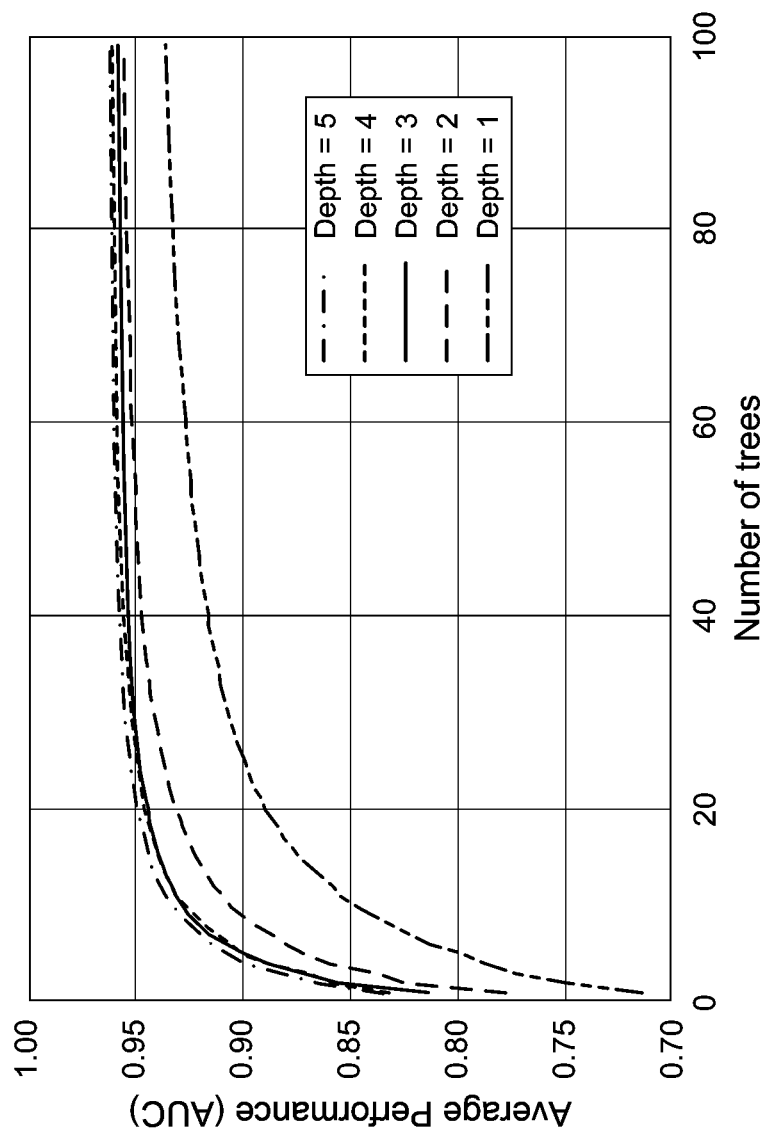
FIG. 6 shows an overall classification performance at various depths versus number of trees.

Decision trees are very efficient, but also susceptible to overfitting in problems with high feature-space dimensionality. To address this, the number of nodes is limited in each tree, i.e., design shallow trees using small number of features. Shorter trees are also more efficient in hardware and incur less detection delay. FIG. 6 shows the area under the curve (AUC) performance of an ensemble of gradient-boosted trees versus the number of trees for different values of depth parameter. An important observation is that the detection accuracy is not significantly improved (<0.5%) with depth values of 4 and higher. Besides, an AUC higher than 90% is achieved using fewer than 10 trees of depth 3 or 4. Therefore, the total energy can be minimized by limiting the number of trees and depth, which are respectively chosen as 8 and 4 in this patent document.

D. Performance and Comparison

Figure 7A:
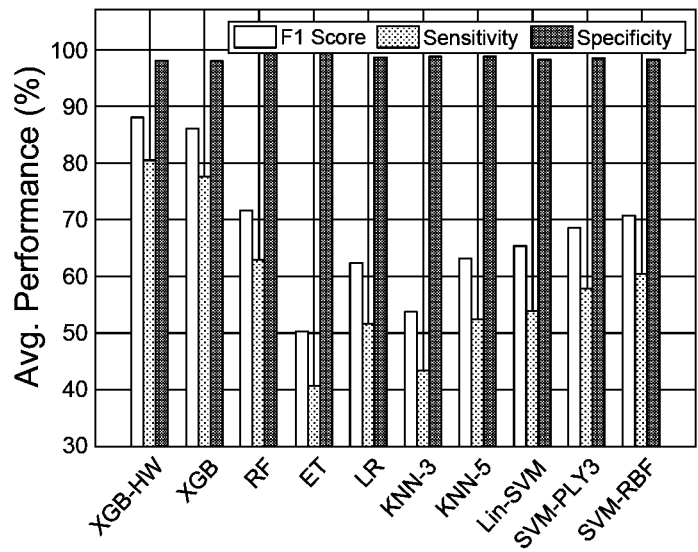
FIGS. 7A and 7B show a comparison of average predictive ability (F1 score), sensitivity, and specificity of different classification methods among patients, using blockwise, and random splitting methods, respectively.
Figure 7B:
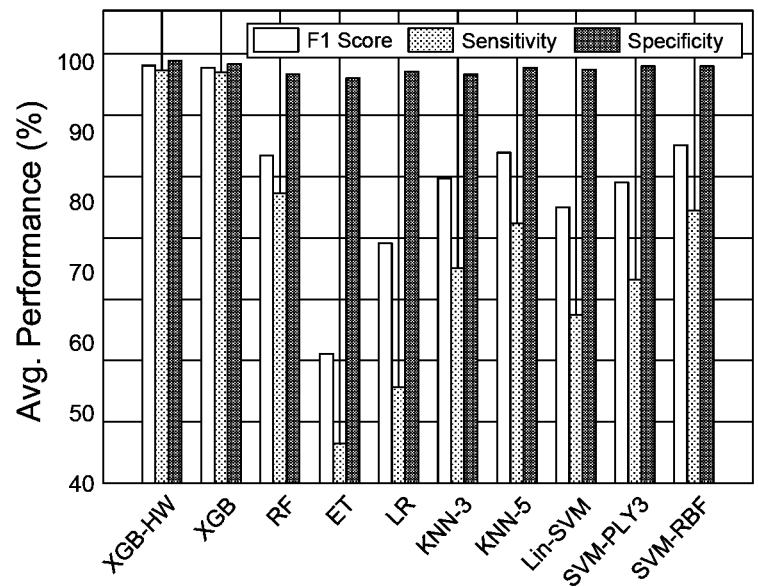

The average performance of classifiers across patients are shown in FIGS. 7A and 7B, using block-wise and random splitting methods, respectively. As mentioned before, due to correlation of iEEG waveforms, random splitting can allow the model to learn from parts of test data and statistics of unseen seizures during training. Therefore, it creates overly optimistic predictive models and invalidates the estimated performance. In this patent document, block-wise approach is considered to alleviate the leakage problem. The F1 score is calculated by counting the number of correctly classified windows, given by:

$$F_1 = \frac{2}{\frac{1}{\text{Sen.}} + \frac{1}{\text{Prec.}}} \quad (6)$$

where sensitivity (Sen.) and precision (Prec.) represent the true positive rate and positive predictive value, respectively. The asynchronous XGB (XGB-HW) performs best among all classifiers, reaching an average F1 score of 99.23% and 87.86%, for the random and block-wise splitting methods, respectively, with an average block-wise sensitivity of 80.33% and specificity of 98.12%.

Figure 8:
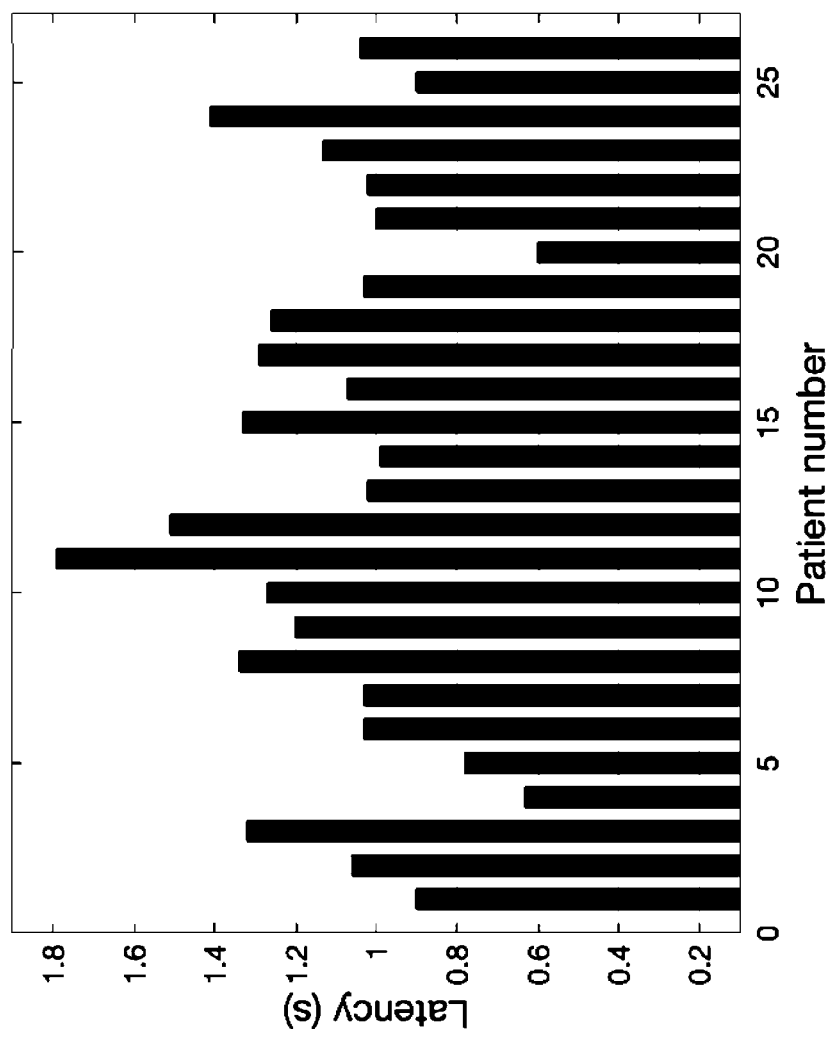
FIG. 8 shows a detection latency of XGBoosted hardware (XGB-HW) across patients.

This is achieved by efficient design of the learning algorithm in an asynchronous online fashion, while minimizing the hardware resources and energy. As expected, random split leads to higher, but unrealistic predictive accuracy. Interestingly, only tree-based methods, in particular, the XGB could classify patient 21's seizures (87% F1 score), while all other classifiers failed for this patient. Random forests generally require a large number of trees to obtain a high performance, which is not suitable for on-chip implementation. The results indicate that the proposed asynchronous gradient-boosting method with as low as eight trees, has a higher generalization ability on this iEEG dataset, compared to methods such as k-NN, LR, and SVM. The performance could be further boosted by artifact removal, as some datasets (e.g., patient 13) are contaminated by high-frequency artifacts that particularly overlap with FR band. To evaluate the detection latency, the number of correctly classified ictal windows is counted at the beginning of a seizure, and wait for at least three consecutive seizure decisions to remove the effect of transient noises. FIG. 8 shows the detection latency of XGB-HW among patients, with an average of 1.1 s.

E. Examined Features

Figure 9:
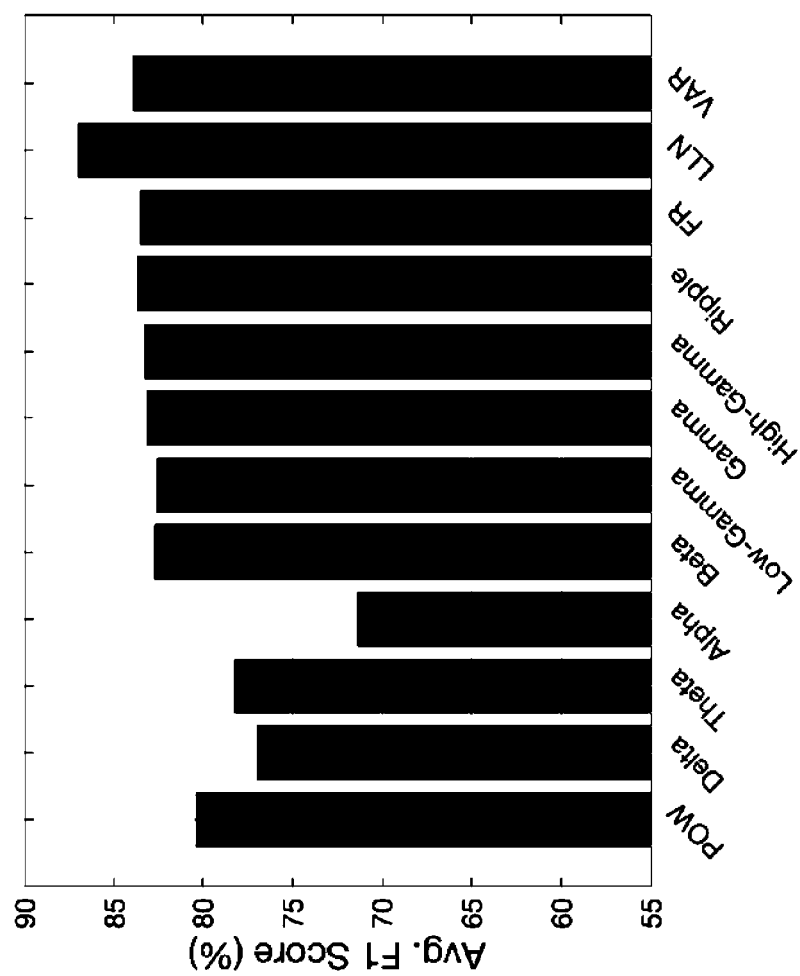
FIG. 9 shows an overall feature importance for the proposed classifier.

FIG. 9 summarizes the overall performance of examined features across patients. Line-length stands out as the best feature, in accordance with many other studies. Variance, ripple, and fast ripple are next. Interestingly, a clear shift is observed in discriminative performance of spectral power features from Berger bands toward gamma, ripple, and fast ripples (all normalized). However, to distinguish between seizure and non-seizure data, both dominant and less dominant frequency components are required, as well as the spatial variation among channels, that is achieved through a multichannel analysis. In this patent document, a programmable filter is implemented with flexible bandwidth settings to cover all seizure-related frequency components. By using a single filter architecture with programmable bandwidth, the hardware complexity of FEE is significantly reduced compared to conventional technology that integrate multiple parallel bandpass filters.

V. EXAMPLES OF SOC IMPLEMENTATION

Figure 10A:
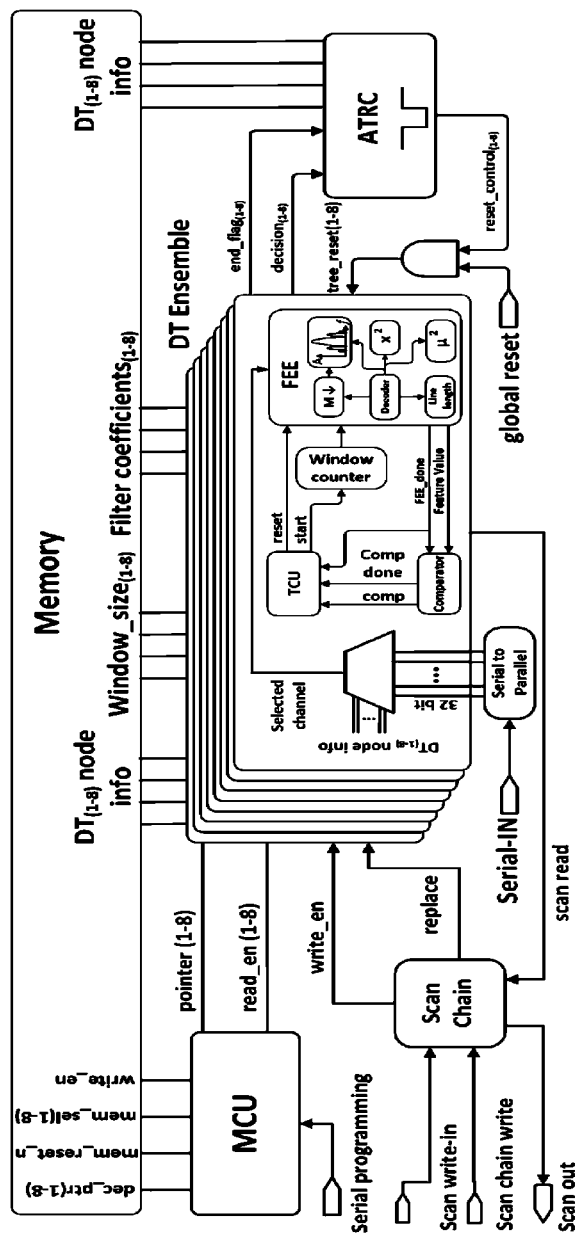
FIGS. 10A and 10B respectively show a block diagram of the implemented system on a chip (SoC); and Power breakdown, die micrograph, and area breakdown of a single tree and feature extraction engine (FEE).
Figure 10B:
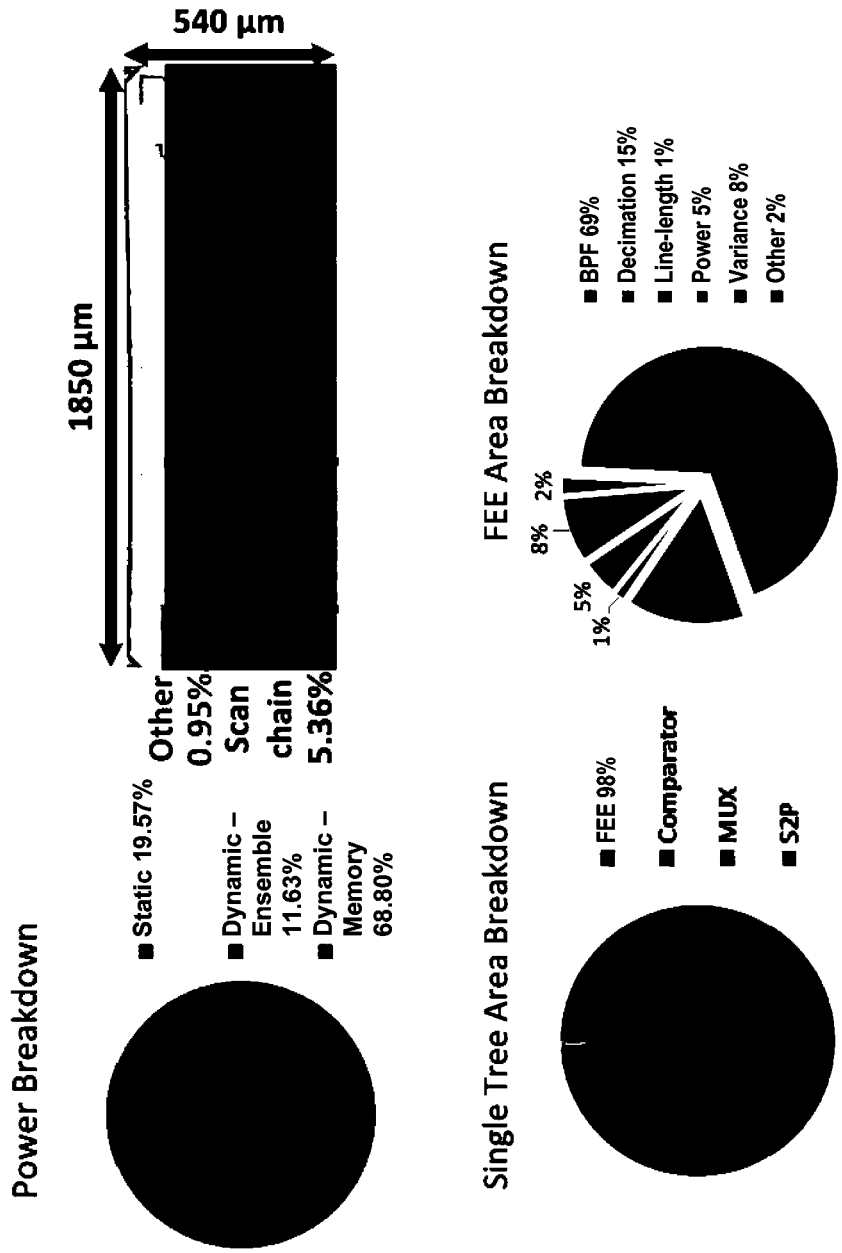

FIG. 10A shows the block diagram of the implemented SoC based on the asynchronous XGB classifier presented in Section III. This classifier supports up to 32 neural channels. One fully programmable feature extraction unit is used per tree and controlled by the Tree Control Unit (TCU) to extract epileptic biomarkers. A Mealy FSM implementation of the closed-loop system is chosen, that substantially reduces the power and area overhead. To extract spectral density features, a single FIR filter structure is used and its coefficients are multiplexed according to the feature or characteristic being processed, thus reducing the total area. As a result, the classifier achieves an energy efficiency of 41.2 nJ/class in a small area of 1 mm2. Features of line-length, variance, and total power are implemented with standard digital logic according to their mathematical definitions in Table I, and contribute to a small portion of feature extraction area (<15%), as shown in FIG. 10B. The main blocks of the implemented Mealy FSM include the ensemble of 8 DTs with programmable FIR filters, a Memory Control Unit (MCU), and an Asynchronous Tree Reset Control (ATRC). The detailed functional description of these blocks is discussed as follows.

1) DT Ensemble: The ensemble includes 8 decision tree structures with a maximum depth of 4 (e.g., maximum of 15 nodes or 15 processing units). For each tree, TCU sets the next state's memory pointer according to the current state, comparator status, and internal flags. A multiplexer selects one channel from the 32-channel input data, according to the current state. This channel is then fed to FEE. At the last processing node of each tree, TCU sends out the 'tree-end' flag as well as final node info to ATRC. Epileptic features are computed in the FEE module. A decoder activates/deactivates its sub-modules according to the feature under study at the current node.

2) Programmable FIR Filters: To calculate spectral power features, a cascade of two FIR stages is implemented in an exemplary hardware of FIG. 2. The first stage decimates or downsamples input samples, while the second stage provides bandpass filtering. Each stage may be bypassed according to selected feature. Since at each node of a tree only one feature may be processed, a single filter structure with programmable coefficients can be used. This would significantly relax the area-power constraints in feature extraction module. The FIR filters have Type-I direct symmetric structures with 7 and 35 taps for the first and second stages, respectively. A direct symmetric structure enables using half the multipliers needed for a standard FIR filter, as well as 50% saving in coefficient memory. A high number of taps would lead to extra power and area in FEE and memory. To select optimal number of taps, extensive analysis was made. Given the importance of higher frequency features in seizure detection as shown in FIG. 9, a particular focus was applied on the required accuracy for capturing low-amplitude ripple and fast ripple features (i.e., HFOs) with short duration and rare occurrence. Thus, the filter architecture and length were chosen to ensure lower than 5% error in HFO extraction over the entire training set.

3) Memory Control Unit: MCU monitors the read/write access to the memory. In the write mode, a decoder activates different memory sub-modules for programming through the serial input, that is generated during patient-specific training. The filter coefficients and prediction model are stored in memory. The fully programmable memory allocation enables a patient-specific seizure detection. In one implementation, the total size of the register type memory is less than 1 kB, with shared filter coefficients using 228 B. The memory associated with filter coefficients may be shared among trees. Thus, in some embodiments, the memory is not linearly scaled by increasing the number of trees. Each DT can have a dedicated 690 b of memory for its node information (690 B for 8 trees). Four sub-memory blocks with a depth of 15 store the tree structure, including each node's feature/channel selection, decimation filter selection, threshold, and leaf values, tree structure (whether there is a child node or not), and window size for feature extraction.

In the read mode, MCU receives pointer address and commands from each DT, and sends back the requested information. It also activates/deactivates the associated filter coefficients from memory to DTs, according to the corresponding node info. Trees work independently in a parallel fashion, using an Asynchronous Tree Reset Control.

4) Asynchronous Tree Reset Control: To effectively capture all abnormalities in the data, each tree works independently and computes its trained features to maximize the accuracy, regardless of computational delay. When the 'tree-end' flag of a tree is raised, ATRC stores the tree status and resets it to the initial state. After reset is cleared, the tree starts processing of new input data. ATRC holds the tree status until the next available 'tree-end' flag. Finally, ATRC assigns each tree's respective leaf values to calculate $D_{final}$ according to (5).

Input precision: The input bit precision should be sufficiently high to ensure the detectability of weak high-frequency features. At least 12-bit resolution may be required to extract correct FR patterns for seizure onset detection. On the other hand, lower bit resolution is preferred to reduce the chip area and power. To find the required number of bits, HFOs from various patients were calculated at 9-12 bit precisions of input data, and compared to those extracted from ideal floating point input. With some extra margin that accounts for lower effective resolution of ADC, 12 bits was chosen because it can enable less than 0.1% error in the amplitude of HFOs.

Experimental setup and measurement results: The chip micrograph of the proposed classification architecture fabricated in a 65 nm semiconductor process and its area breakdown are depicted in FIG. 10B, as well as the area breakdown of a single tree and the FEE. Each tree, including its dedicated and shared memory units, takes 11.25% of the die area. FIG. 10B also shows the power breakdown of the proposed SoC operating at a 0.8V supply, with an energy efficiency of 41.2 nJ/class. Power measurements were made at worst-case scenarios where all the internal registers are switching and FEE is saturated (i.e., electrical onset of seizure is approaching).

Figure 11:
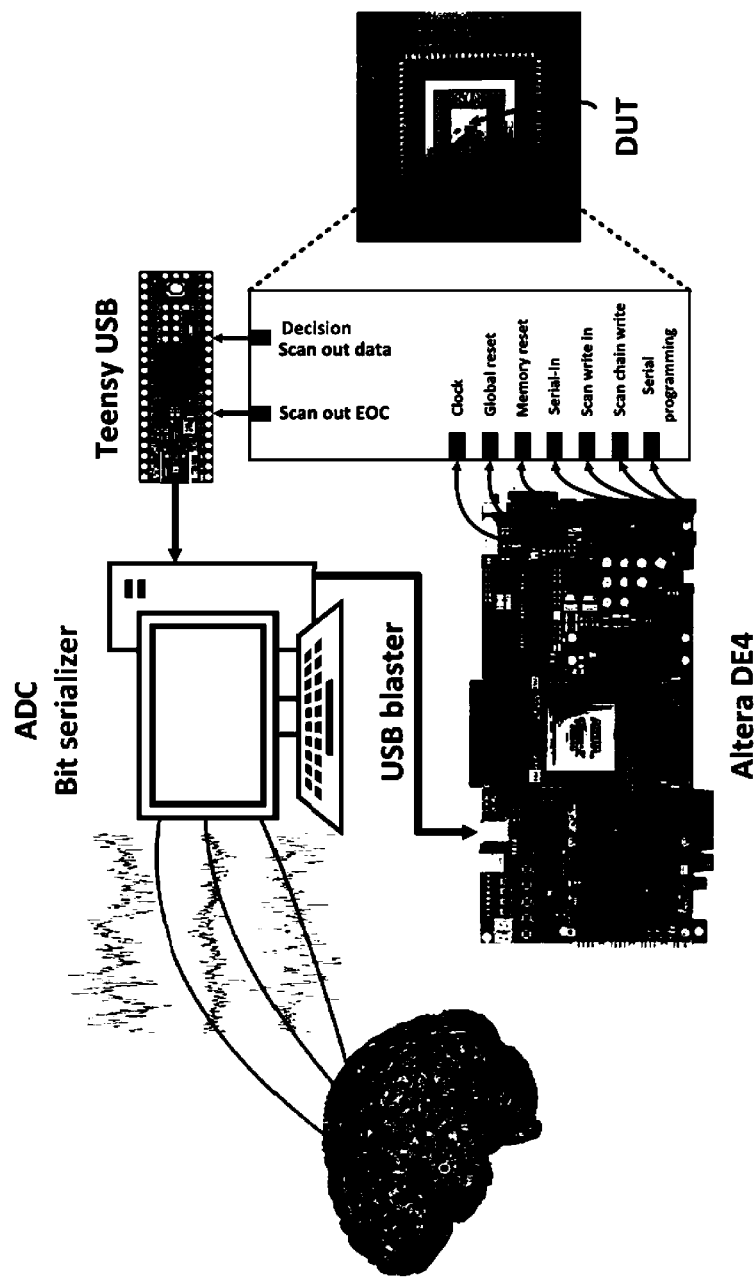
FIG. 11 shows an experimental setup to measure the on-chip classifier.

In order to test the seizure detection performance of the fabricated chip, iEEG recordings from epileptic patients were digitized on a local PC with 12-bit resolution. The digitized data of all channels were then serialized and stored on the DDR2 SDRAM of an Altera DE4 board, as shown in FIG. 11. The information of prediction model was serially sent to the Serial Programming input of the implemented SoC (shown on the right). Once the prediction model is stored on memory, FPGA provides input clock and start command to SoC. For each patient, the chip is programmed according to the ensemble structure of his/her trained prediction model. Then, the test iEEG data of that patient is loaded to the chip for feature extraction and classification.

Using the measured decisions, sensitivity and specificity are calculated. The chip was tested with 2253 hours of iEEG data from 20 patients. As the chip handles up to 32 input channels, those patients with up to 32 channels in their trained prediction model were used for the test. Given the limited data storage on FPGA, up to 10 hours of iEEG data was used for each test. The exact duration was determined based on the state of iEEG data. In the case of significant seizure-like activity in the vicinity of 10 hour, the duration of test data was reduced to 9 hours, with the last 1-hr added to the following experiment. Table II summarizes the performance of the exemplary system described in this patent document (referred to as "this work") compared to the state-of-the-art on-chip classifiers for seizure detection. In measurements, the classifier achieves an average sensitivity and specificity of 83.7% and 88.1%, respectively. For a fair comparison with state-of-the-art, energy and area are normalized to the 65 nm technology node. The proposed architecture achieves over 27× improvement in energy-area-latency product.

they only scale up with number of trees and do not pose excessive memory and hardware requirements. Without any channel selection or feature reduction techniques (that is required in most traditional methods due to large dimension of features), the proposed classifier inherently selects an optimal set of channels and related features that form the tree structure. Thus, one of the main contributions of this patent application is a hardware approach to enable energy reduction by minimizing the number of simultaneously extracted features, thus breaking the energy-area vs. accuracy tradeoff. Buffer-less processing of data in a closed-loop scheme is employed, and programmable bandpass filters further decrease the overall area overhead. The total power can be further reduced by dynamically controlling the channel activation and powering down the low-noise amplifiers in unused channels.

A. Energy-Quality Tradeoffs and Scaling

In the exemplary proposed gradient-boosting classifier, each tree contributes to roughly 10% of total power (static and dynamic). Based on the performance curves shown in

TABLE II

SoC Performance and Comparison

| Parameter | ISSCC'13 [16] | JSSC'13 [15] | JSSC'14 [17] | JSSC'13 [18] | This work |
|---|---|---|---|---|---|
| Process | 180 nm | 180 nm | 180 nm | 130 nm | 65 nm |
| Classifier | Non-Lin SVM | Lin-SVM | LLS | SVM‡ | XGB |
| Signal Modality | EEG | EEG | iEEG | EEG | iEEG |
| Channel Count | 8 | 8 | 8 | 18 | 32 |
| Energy Eff. | 1.23* μJ/class | 1.52* μJ/class | 77.91 μJ/class | 273 μJ/class | 41.2 nJ/class |
| Logic Size† | 2.27M | 3.3M | N.A. | 371k | 330k |
| Memory [kB] | N.A. | N.A. | N.A. | 32§ | 1 |
| Area | 7 mm²* | 8.18 mm²* | 6.5 mm²* | 5.13 mm² | 1 mm² |
| Sensitivity [%] | 95.1 | N.A. | 92 | N.A. | 83.7 |
| Specificity [%] | 94 | N.A. | N.A. | N.A. | 88.1 |
| Latency [s] | 2 | 2 | 0.8 | N.A. | 1.79†† |

*Area and Energy Efficiency conservatively estimated from A/P breakdown
†Number of equivalent NAND2 gates with driving strength of one
‡Linear, Polynomial, RBF
§32 kB SV MEM, 16 kB Programming MEM, 16 kB Data MEM
††Worst case latency (patient 11)

VI. SCALABILITY AND HARDWARE OPTIMIZATION

The small number of channels in existing neural interface technology remains a barrier to the therapeutic potential. For instance, the spatial coverage and resolution of electrodes has a high impact on the detection accuracy of epilepsy implants. The exemplary proposed XGB classifier in this patent document can be scalable to multi-sensor and multi-channel operation, through sharing the computational and memory resources for feature extraction and classification among channels. In contrast to a majority of other classifiers that linearly scale in computational and memory requirements with number of channels and features, the proposed classifier can compute a handful of features per tree, regardless of total channel count. This approach enables significant savings in computational resources and required storage on chip.

Figure 12:
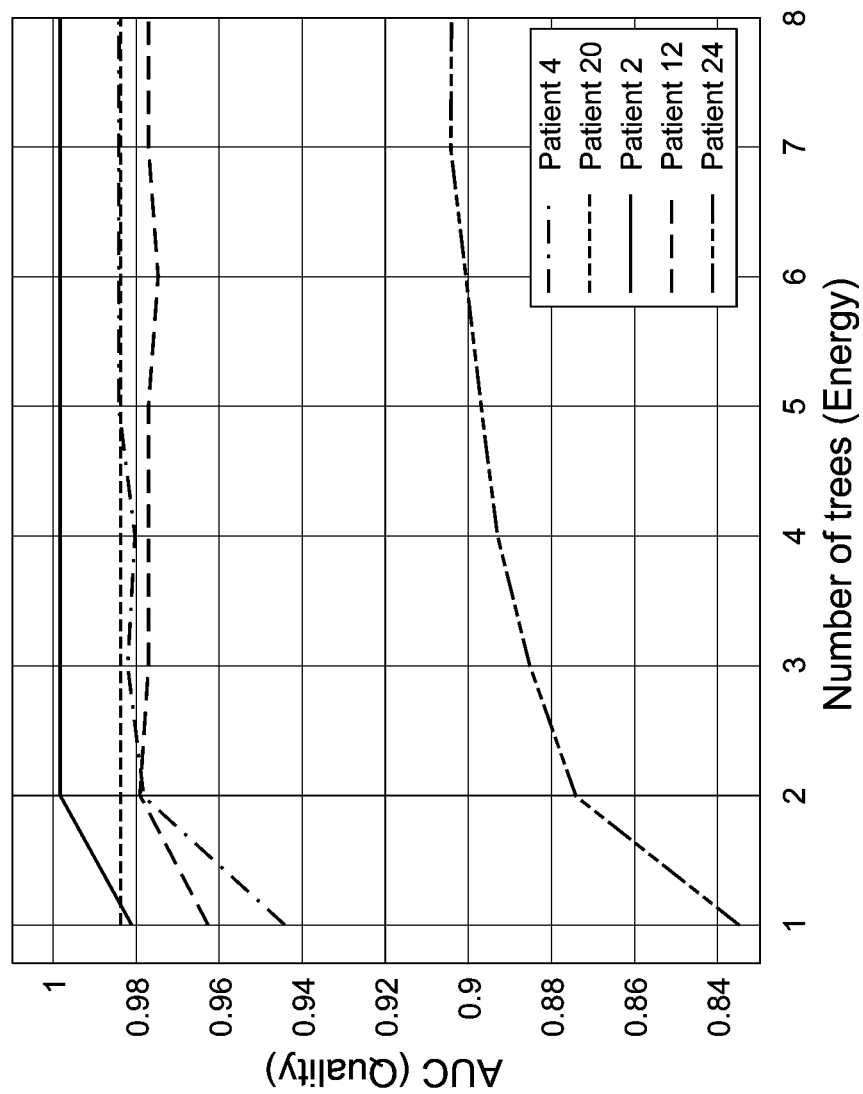
FIG. 12 shows a measured area under curve (AUC) versus number of trees for various patients.

Although a relatively simple feature set is chosen and described in this patent document, one may use additional complex and non-linear features to boost the accuracy at a negligible cost. The total number of feature extraction units to be physically placed on chip is proportional to number of trees, while only one feature is computed in each tree at a time, saving both power and area. In other words, as many features can be included as the application requires, since FIG. 6, an ensemble of eight trees with a maximum depth of four was implemented, to achieve an average AUC of more than 90% across a large population of patients with varying number of electrodes, seizures, and sampling rates. However, not all patients in the database need as many trees for an accurate discrimination of their seizures, as depicted in FIG. 12 (top curves). Therefore, a programmable on/off control was enabled for each tree in the ensemble, so that upon a patient-specific training phase, one or more trees could be switched off to save power, with a minimum impact on quality. In other words, depending on the difficulty of detection task, the required number of trees can be switched on to achieve an expected classification accuracy (e.g., eight trees for patients with hardly detectable seizures, such as patient 24 in FIG. 12). The AUC is used as the quality metric, that is widely used to evaluate the predictive accuracy of a classifier.

Boosting methods generally attain high discrimination by sequential training of weak classifiers. Here, the XGB attempts to increase the predictive accuracy by making a more accurate prediction at each iteration. However, increasing the number of DTs increases the memory and power requirements of the system. The proposed XGB hardware is inherently quality-scalable through programming the number and depth of the active trees, with a maximum depth set at four. Moreover, the design offers a unique flexibility to accommodate various tree structures specific to each patient, to trade the predictive accuracy with energy (i.e., avoid unnecessary energy dissipation when accuracy is just enough for a patient). The hardware parameters of tree count and depth across all patients were explored as potential knobs for energy-quality scaling.

As shown in FIG. 12, in most patients, a small number of trees are sufficient for a reliable seizure detection. Indeed, the structure of successive trees are very similar in most patients, and by switching off the last few trees, only a slight decrease in predictive accuracy was observed. While chip area is limited by the required number of trees for worst case patients, the energy usage can be scaled for cases with easily detectable seizures. The other alternatives (knobs) for energy-quality scaling include pruning of trees, or forcing the algorithm to use energy-aware features by modifying the cost function (i.e., adding an energy constraint similar to the delay constraint in FIG. 4). However, for most patients, the very last 3-4 trees in the iterative training process of XGB have a slight impact on performance and could even cause overfitting. In addition, the proposed asynchronous approach requires a single FEE in each tree that freely runs to compute one feature at a time. Thus, its energy is less sensitive to the depth parameter and is rather controlled by sampling frequency. Thus, the hardware knob of tree count can be easily integrated into the power-aware classification prototype.

B. Discussion on Hardware Optimization

Various opportunities to improve the energy and area efficiency of proposed classifier could be further explored. For instance, the input bit precision in the chip implementation has been chosen sufficiently high to allow the detectability of high-frequency features. Given the inherent error tolerance in machine learning algorithms, the energy per classification can be reduced by relaxing the quality or precision of features. For low-power and compact implementation in particular, reducing the resolution of coefficients in filter banks, feature thresholds, and leaf values is critical. New approaches to train decision trees with fixed-point and low-cost parameters can be investigated, similar to the techniques that reduce precision in DNNs, SVMs and LRs. Since the training is usually performed offline, the associated cost is not critical. Such parameters could further be used as potential knobs in the proposed energy-quality scaling framework.

Furthermore, DTs can be trained to incorporate the costs of misclassification (FP or FN) and feature computation (power, area, delay) in the tree induction process. For example, it is critical to achieve a high sensitivity in seizure detection, while keeping the false alarm rate and latency below a tolerable level. This can lead to development of cost-sensitive decision trees, where the top-down tree induction algorithm may be adapted to maintain a pre-specified cost, therefore trading off the unnecessary accuracy (e.g., very high specificity or low latency) and energy. Besides, using various design parameters of DTs, the XGB classifier can be programmed to trade energy and quality in a structured and dynamic fashion.

VII. CONCLUSION

In this patent document, the challenge of designing a low-power machine learning algorithm for on-chip neural data classification is addressed. An exemplary hardware architecture is proposed for a gradient-boosted decision tree model, with a single feature extraction engine and programmable FIR filter per tree. The proposed asynchronous tree operation enables efficient classification of multichannel neural data, with significantly lower memory, power and area requirements compared to state-of-the-art. As a result, this on-chip classifier achieves an energy-area-latency product that is 27× lower than prior techniques, while processing the highest number of channels. The hardware architecture, design optimization and tradeoffs are discussed, and algorithm performance based on proposed model and SoC measurements is presented. Such classifiers could potentially allow full integration of processing circuitry with the sensor array in various resource-constrained biomedical applications.

VIII. IMPROVED DETECTION OF PARKINSONIAN RESTING TREMOR WITH A MACHINE LEARNING APPROACH

In Sections VIII.1 to VIII.5, multiple features of local field potentials in subthalamic nucleus were investigated to detect resting tremor in Parkinson's disease, the use of relevant features, machine learning, and Kalman filter is shown to improve the tremor detection performance, and the Kalman filter in feature space is shown to significantly improve the specificity of detection by 17%.

Accurate and reliable detection of tremor onset in Parkinson's disease (PD) is critical to the success of adaptive deep brain stimulation (aDBS) therapy. Here, we investigated the potential use of feature engineering and machine learning methods for more accurate detection of rest tremor in PD. We analyzed the local field potential (LFP) recordings from the subthalamic nucleus region in 12 patients with PD (16 recordings). To explore the optimal biomarkers and the best performing classifier, the performance of state-of-the-art machine learning (ML) algorithms and various features of the subthalamic LFPs were compared. We further used a Kalman filtering technique in feature domain to reduce the false positive rate. The Hjorth complexity showed a higher correlation with tremor, compared to other features in our study. In addition, by optimal selection of a maximum of five features with a sequential feature selection method and using the gradient boosted decision trees as the classifier, the system could achieve an average F1 score of up to 88.7% and a detection lead of 0.52 s. The use of Kalman filtering in feature space significantly improved the specificity by 17.0% (p=0.002), thereby potentially reducing the unnecessary power dissipation of the conventional DBS system. Thus, the use of relevant features combined with machine learning and Kalman filtering can improve the accuracy of tremor detection during rest. The proposed method offers a potential solution for efficient on-demand stimulation for PD tremor.

VIII.1. Introduction

Deep brain stimulation (DBS) is a widely utilized treatment option to reduce the motor symptoms of advanced PD such as resting tremor, akinesia, and rigidity. Conventional DBS delivers constant and high-frequency (~130 Hz) stimulation pulses which may cause side effects such as psychiatric symptoms and speech impairment. Moreover, open-loop charge delivery increases the power consumption of the DBS system, potentially requiring a surgical battery replacement every three to five years. To address these challenges, the so-called adaptive DBS (aDBS) approach offers a promising alternative, by replacing conventional stimulation with a closed-loop and adaptive one. In this approach, the neuromodulation is dynamically controlled by motor symptoms such as tremor or bradykinesia, either in a continuous way, or with an on-off strategy. By providing feedback from relevant biomarkers, such as the beta band power of LFPs in the subthalamic nucleus (STN), adaptive DBS can titrate stimulation, hence reducing the total stimulation delivered, improving both the efficacy of treatment and side effects, and increasing the battery life. Proof-of-concept studies of adaptive DBS in humans have reported promising advantages over conventional DBS, including a 27% improvement of the Unified PD Rating Scale (UPDRS), 56% reduction of stimulation time and energy dissipation, and improved speech intelligibility. The adaptive DBS method tested used feedback based on the beta amplitude of LFPs recorded by the stimulation electrodes.

In order to characterize motor symptoms in PD, biomarkers in the LFP of STN and GPi have been studied. For instance, neuronal oscillations within the motor network and over the tremor frequency range (~3-7 Hz) have been shown to correlate with resting tremor, measured as increased cortico-muscular coherence during tremor. The beta band (13-30 Hz) power in the cortex and STN has been shown to reduce during PD rest tremor, while the cortical beta phase-amplitude coupling with broadband gamma oscillations (50-200 Hz) decreases during rest tremor. The ratio of high-frequency oscillations (HFOs) between the slow band (200-300 Hz) and the fast band (300-400 Hz) has also been shown to increase during rest tremor. Moreover, the low gamma (33-55 Hz) power in the STN LFP is increased during rest tremor in Parkinson patients. While such features can potentially be used for real-time detection of resting tremor, the majority of current adaptive DBS experiments have been overly simplistic and based on a single feature such as beta band power, with a simple thresholding mechanism to control DBS. However, the exclusive usage of beta-band power in the STN may not be optimal for tremor detection in PD, given that it is not correlated with tremor. Therefore, other relevant biomarkers of pathological neural activity and powerful classification algorithms need to be investigated to more accurately characterize and predict the tremor state.

To improve resting tremor detection from the LFP, a multi-feature classification approach based on features of the LFP such as variance, zero crossing rate, autocorrelation, band powers, and wavelet transform has been used to identify tremor related characteristics in PD patients, and shows that LFPs from STN or GPi provide sufficient information for rest tremor detection. In another study, using beta, gamma, and tremor band powers, the ratio of slow and fast high frequency oscillations (HFOs), and a Hidden Markov Model (HMM), the Parkinsonian rest tremor was also accurately detected from STN LFPs. Both frequency and time domain features such as multiple band powers and the Hjorth parameters from subthalamic LFPs, combined with a logistic regression classifier have also been used to detect Parkinsonian rest tremor. However, despite promising results, the latency of tremor detection was not reported in these studies, and can be an important parameter for implementation of closed-loop DBS where stimulation should best anticipate symptomatic disturbance. Furthermore, the use of more domain-specific features and advanced machine learning techniques may further improve the tremor detection accuracy. In various other neurological applications such as seizure detection for medication-resistant epilepsy and movement intention decoding in brain-machine interface systems, the use of machine learning and domain specific features has made a significant impact by achieving remarkable accuracies. Particularly, gradient boosting-based algorithms such as XGBoost have been very successful in classifying time-series neurophysiological data with limited training sets and have been included in our analysis. Such decision tree-based classifiers have been recently integrated on microchips with ultra-low power consumption and small area utilization and could potentially be used for hardware implementation of aDBS. Moreover, the evaluation of tremor detection algorithms in a greater number of patients with different tremor characteristics is another crucial step for the reliability assessment of aDBS and its translation to a clinical setting.

This patent document describes research of the predictive accuracy of various biomarkers in the LFP recorded in the region of STN, such as band power in relevant frequency bands, beta-HFO phase-amplitude coupling (PAC), the Hjorth parameters that have been primarily used for EEG characterization, and wavelet entropy. We evaluate these neurophysiological biomarkers for quantifying Parkinsonian rest tremor in a group of 12 PD patients with different tremor intensities, and employ advanced ML models to detect rest tremor periods. Moreover, to further enhance the tremor detection performance, a Kalman filtering approach in the feature domain is explored.

VIII.2. Materials and methods

Figure 14:
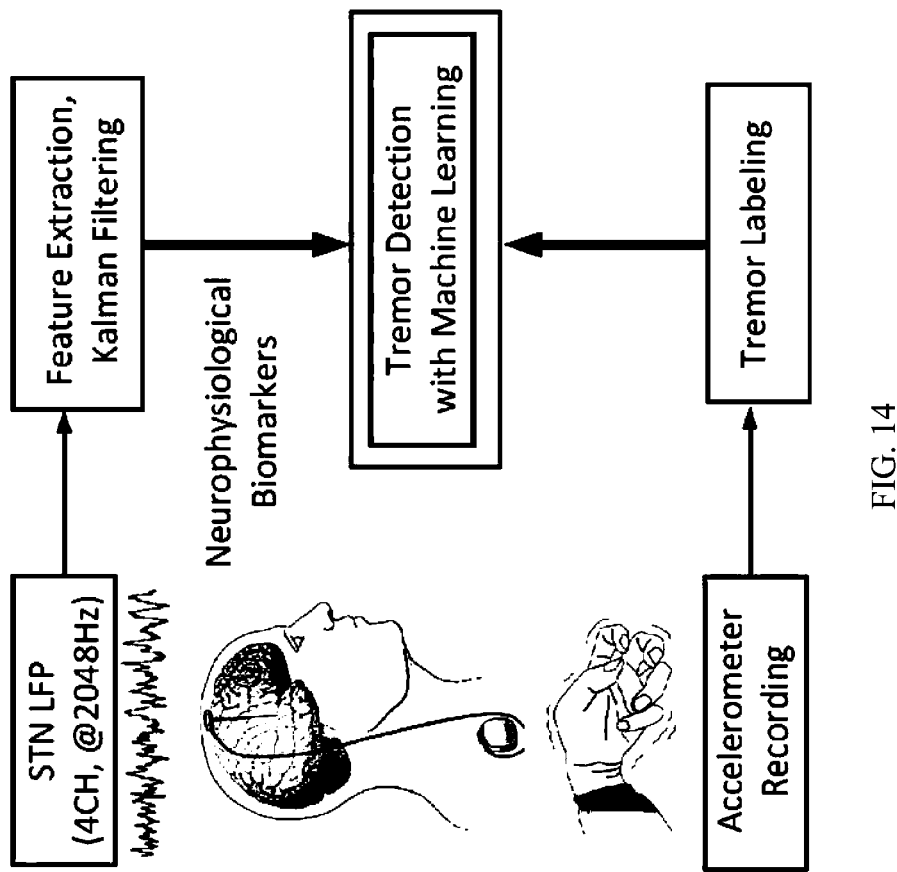
FIG. 14 shows an overview of the proposed framework for tremor detection where the output of machine learning-based classifier can be used to activate DBS in an envisioned closed-loop system.

The overview of our proposed framework for tremor detection is depicted in FIG. 14. The goal is to accurately detect the occurrence of resting tremor by directly measuring the neural activity in STN. We opted to detect tremor from the LFP rather than from peripheral inertial signals as then stimulation could potentially anticipate the physical symptom. In addition, wireless communication between peripheral sensors and an internalized system introduces potential vulnerability to hacking, and additional energy demands. We used a supervised learning approach to classify the continuous LFP signal, while simultaneous measurements from an accelerometer sensor were used to label the data, as 'ground truth'. The neurophysiological biomarkers were extracted from multi-channel LFP signals and a Kalman filter was used to process the extracted features. We subsequently trained different classifiers on a labeled feature set and evaluated the trained models on the test set to detect the tremor and non-tremor states.

2.1. Patients and Surgical Procedure

We studied 12 PD patients recruited from the University of Oxford. All subjects gave informed consent to participate, and the local research ethics committee approved the study. Patients were aged between 46 and 73 years old (mean 62 years old, 10 males), and had a disease duration ranging from 4 to 17 years (mean 10 years). Bilateral DBS electrodes were implanted into the STN, preceding the therapeutic stimulation for advanced idiopathic PD with motor fluctuations or dyskinesias. All the studied patients also had resting tremor. Detailed techniques for targeting and implanting electrodes in the STN have been previously reported. Microelectrode recording was not performed during surgery. The model 3389 quadripolar macroelectrode with four platinum-iridium cylindrical contacts was used. The contacts of this electrode range from 0 to 3, with contact 0 indicating the most caudal contact. Electrodes were localized intra-operatively through the effect of direct stimulation, and immediately post-operation by stereotactic imaging. Nevertheless, considering that not all contacts lie in the STN per se, we termed the area sampled by the electrode contact as the STN region (STNr). The extension cables for DBS electrodes were externalized through the scalp, enabling recordings prior to connection to a subcutaneous pacemaker, which was implanted in a second operation a week later. A TMSi porti (TMS international, Netherlands) and associated acquisition software were used to record monopolar LFPs at a sampling rate of 2048 Hz. These were then common average referenced and bandpass filtered between (0.5-500 Hz). Bipolar LFPs were extracted offline, by subtracting the monopolar signals measured by neighboring contacts on each electrode. We included three bipolar channels in our analysis (0-1, 1-2, 2-3). In a separate study, we included the bipolar channels between 0-2 and 1-3 contacts, which is a preferred strategy to reject the stimulation artifact on the middle electrode during adaptive DBS. We also compared the performance of our classifier using a bipolar versus monopolar electrode contact configuration.

Overall, the dataset included 16 LFP recordings (7 from right side), as patients with bilateral tremor were recorded from both hemispheres. The LFPs were recorded from the STNr with both medication withdrawn overnight and DBS off, while the acceleration of the contralateral limb was simultaneously recorded. Patients were at rest throughout the recordings. The LFP recordings varied from 1.5 to 10 (mean 6.2) minutes in duration among patients. Tremor prevalence ranged from 41 to 97 (mean 73) % of time.

2.2. Data Annotation

Figure 15:
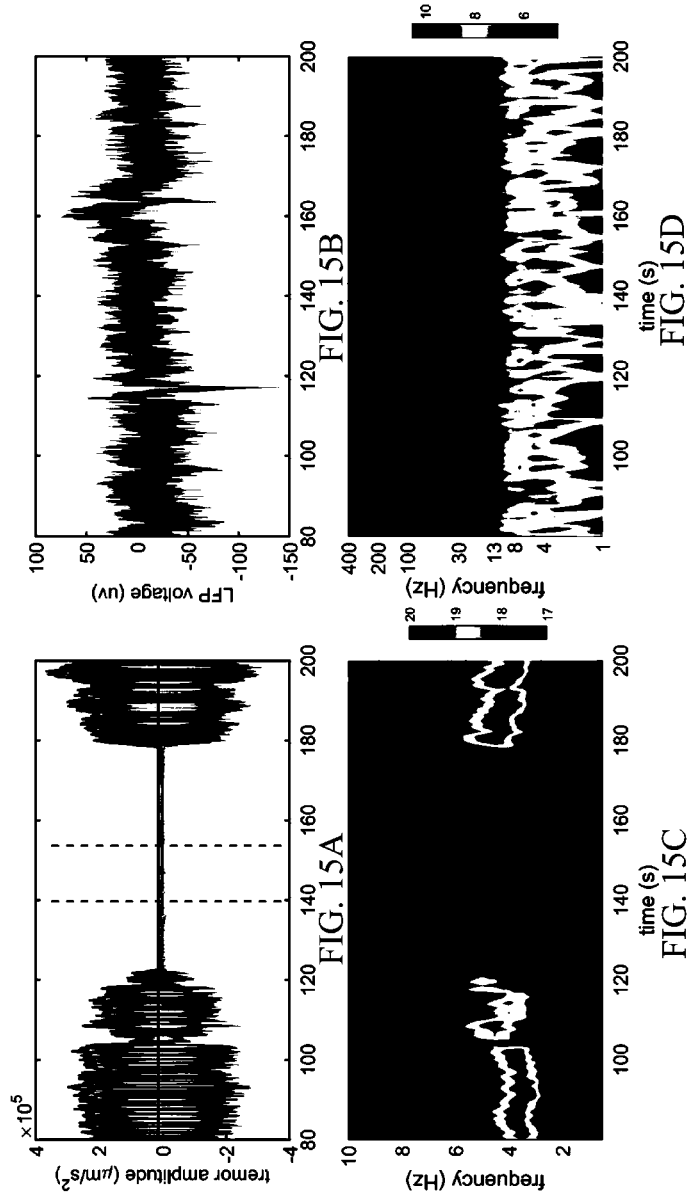
FIG. 15A shows a tremor labeling based on acceleration signal.
FIG. 15B shows a corresponding LFP, where the red curve shows the envelope of the filtered acceleration around the tremor frequency, while the two vertical lines define the non-tremor period as baseline for threshold setting. The horizontal black line represents the threshold to separate the tremor and non-tremor periods.
FIG. 15C shows a time-frequency decomposition of the acceleration signal.
FIG. 15D shows a corresponding LFP (the y-axis is displayed in log scale), where the color bars on the right indicate the log of the absolute power.

In order to label the data, the tremor frequency $f_T$ of the accelerometer recording was calculated as the frequency associated with the highest amplitude (over 1-10 Hz). Then, a Butterworth filter of second-order over the frequency range of ($f_T-1$; $f_T+1$ Hz) was used to filter the acceleration signal from the limb, and a Hilbert transform was subsequently applied to extract the envelope, as shown in FIGS. 15A-15D. We then identified the resting non-tremor period as baseline, through visual inspection. For instance, the interval between the two vertical lines in FIG. 15A is considered as non-tremor. The mean value+five times the standard deviation of baseline was empirically set as threshold, and the envelope was labeled as tremor if its amplitude surpassed the threshold level. While this method was effective in most patients, in some cases (i.e., 5 recordings) we had to slightly adjust the threshold to avoid the unnecessary annotation of very small and short-duration motions as tremor, and avoid rapid label switching within longer tremor episodes.

2.3. Feature Extraction

In order to compute the LFP biomarkers of tremor, we used a 1-second window with half overlapping to continuously segment the LFP recordings. Fifteen features were extracted from the three bipolar channels as described in Table III, forming a 45-dimensional feature vector. In addition to beta power, which is the most commonly used feature in aDBS studies, we explored other potentially relevant biomarkers based on prior research on Parkinson's disease and other neurological diseases, with the goal of improving tremor detection performance. The selected feature set included band power in several frequency bands, phase-amplitude coupling, and time-domain features such as the Hjorth parameters, as outlined below.

TABLE III

Neurophysiological biomarkers for resting tremor detection.

| Biomarker | Description |
| --- | --- |
| 1. Low Beta | Spectral power in (13-20 Hz) |
| 2. High Beta | Spectral power in (20-30 Hz) |
| 3. Low Gamma | Spectral power in (31-45 Hz) |
| 4. Gamma | Spectral power in (60-90 Hz) |
| 5. High Gamma | Spectral power in (100-200 Hz) |
| 6. Low HFO | Spectral power in (200-300 Hz) |
| 7. High HFO | Spectral power in (300-400 Hz) |

TABLE III-continued

Neurophysiological biomarkers for resting tremor detection.

| Biomarker | Description |
| --- | --- |
| 8. HFO Ratio | Power ratio of HFO in (200-300 Hz) and (300-400 Hz) |
| 9. PAC | Phase-amplitude coupling between the phase of beta (13-30 Hz) and the amplitude of HFO (150-400 Hz) |
| 10. Tremor Power | Spectral power in (3-7 Hz) |
| 11. Max Power | The peak power in (3-7 Hz) |
| 12. Wavelet Ent | Wavelet entropy |
| 13. Hjo Act | Hjorth activity |
| 14. Hjo Mob | Hjorth mobility |
| 15. Hjo Com | Hjorth complexity |

2.3.1. Low and High HFO Power

The presence of HFO in STN (~300 Hz) was reported in patients with PD under dopaminergic treatment. It has been further shown that the lower frequency HFO power (200-300 Hz) decreases after levodopa intake, while the higher frequency HFO power (300-400 Hz) increases. Furthermore, the ratio between the low and high HFO powers is shown to be a marker of Parkinsonian resting tremor. This ratio has been shown to increase when tremor occurs.

2.3.2. Phase-Amplitude Coupling (PAC)

The coupling between the beta-band phase and HFO (150-400 Hz) amplitude in STN LFPs has been shown to have a positive correlation with severity of motor impairment, while it decreases after the intake of dopaminergic medication.

2.3.3. Tremor Power and Maximum Peak Power

An increased cortico-muscular coherence during tremor has been observed within (3-7 Hz) frequency range in the motor network. In our study, we extracted both the total power and the maximum peak power in (3-7 Hz) to index the tremor state.

2.3.4. Hjorth Parameters

The Hjorth parameters of a signal describe its statistical characteristics in the time domain and are commonly used in EEG studies. These parameters include the activity, mobility, and complexity. While the Hjorth activity indicates the signal variance, mobility is a measure of the average frequency. Furthermore, the variations in frequency within a given time period are presented by the Hjorth complexity.

2.3.5. Gamma Power

Multi-site LFP recordings from STN have shown an increased low gamma oscillation (31-45 Hz) during strong tremor periods, suggesting that low gamma might be a pertinent feature for tremor detection. We further included the gamma power in a higher frequency band (60-90 Hz) previously reported in STN LFPs, and the high gamma (100-200 Hz) power that has been reported in macaque local field potentials.

2.3.6. Wavelet Entropy

The wavelet entropy can be used to analyze the transient features of a non-stationary signal, while estimating the degree of order or disorder of the signal. It has been a useful tool to analyze EEG signals, and given the difference of power spectrum within tremor and non-tremor states, we hypothesized that the associated wavelet entropy might be a useful feature for tremor detection.

2.3.7. Low and High Beta Power

The beta (13-30 Hz) power measured in the cortex and STN is reduced during resting tremor. Furthermore, the low beta (13-20 Hz) power significantly decreases in the on-state following the administration of apomorphine and levodopa. We included both low and high beta features in our study.

2.4. Correlation Analysis

We used a biserial correlation coefficient to quantify the correlation of each feature with the labeled tremor. This coefficient measures the ratio between the absolute difference of the group means (tremor and non-tremor) and the pooled standard deviation of the two classes. The maximum correlation coefficient of the three bipolar channels was used to represent the correlation of each feature with tremor.

2.5. Kalman Filtering

Figure 16:
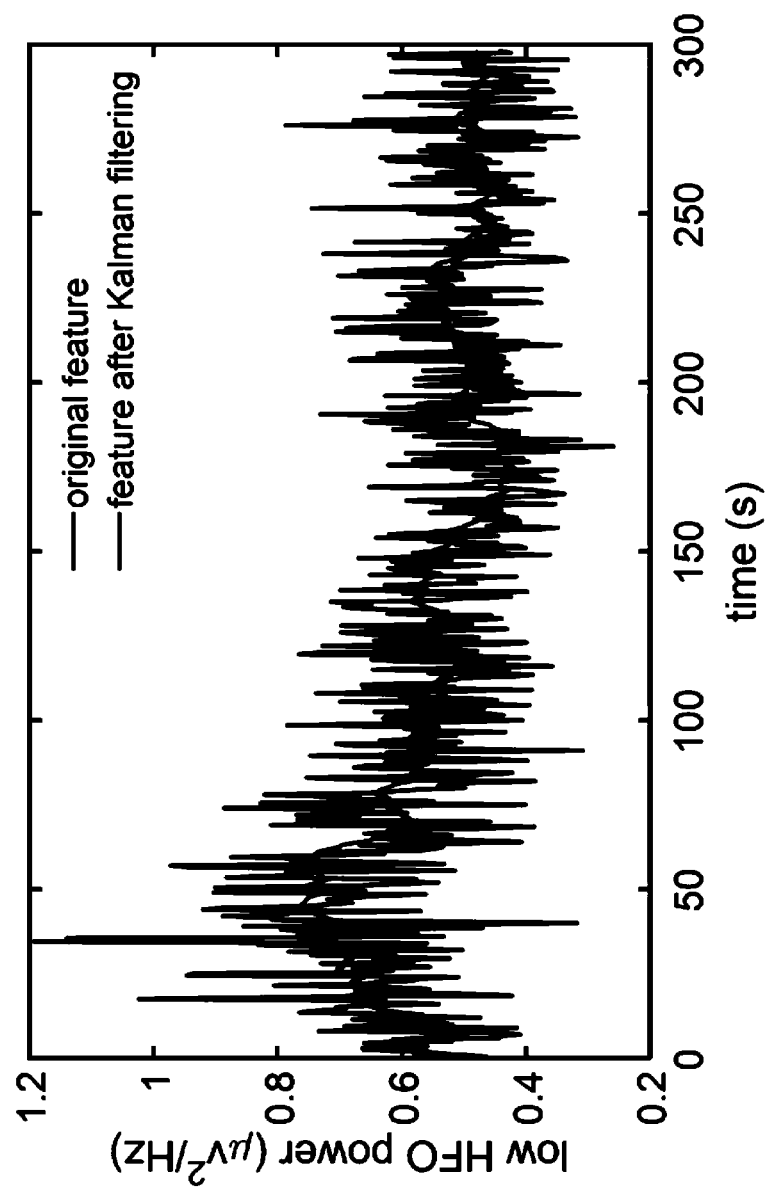
FIG. 16 shows a Kalman filtering in feature space, where the blue curve represents the original feature (low HFO power), while the red curve shows the corresponding feature following Kalman filtering.

The Kalman filter has been used to track the state of a system based on the model of its dynamics and noisy measurements over time. This approach minimizes the variance of the estimation error, thus effectively reducing the undesired fluctuations of the measured data. In tremor detection for PD, the noisy fluctuations of the measured local field potentials and the associated features may degrade the tremor detection performance. As illustrated in FIG. 16, we applied a Kalman filter of second-order to reduce the noise in feature time series and obtain a smoothed feature following Kalman filter. We expected that this approach of using Kalman filter would lower the rate of false positive detections and improve the overall decoding performance. The Kalman filter can be located in the Feature Ext. & Comp. block in FIG. 2. For example, in FIG. 2, the Kalman filter can be included after the feature extraction engine and before comparator. The output of the FIR filter or feature extraction engine is sent to the Kalman filter. A brief summary of the filtering process is provided below.

Assuming that $[d_k \dot{d}_k]^T$ represents the state vector $v_k$, where $\dot{d}_k$ denotes the derivative of $d_k$, the feature vector $f_k$ is described by the following state-space model:

$$\begin{cases} v_{k+1} = \begin{bmatrix} 1 & T_p \\ 0 & 1 \end{bmatrix} \times v_k + w_k \\ f_k = [1\ 0] \times v_k + u_k \end{cases} \quad (7)$$

where $T_p$ shows the time interval of the prediction and $w_k$ represents the process disturbance, assumed to be a white noise of zero mean and covariance of:

$$Q = \begin{bmatrix} \sigma_w^2 \frac{T_p^3}{3} & \sigma_w^2 \frac{T_p^2}{2} \\ \sigma_w^2 \frac{T_p^2}{2} & \sigma_w^2 T_p \end{bmatrix} \quad (8)$$

The Kalman filter is applied to the model in (7) to recursively provide an estimate $\hat{d}_k$ of $d_k$. Next, the obtained smoothed variable $\hat{d}_k$ is utilized in place of $f_k$ as input to our machine learning model. The standard deviations $\sigma_w$ of $w_k$ and $\sigma_u$ of $u_k$ are the required parameters for Kalman filtering, while the Kalman gain depends on $\sigma = \sigma_w/\sigma_u$, which is set to $5*10^{-5}$ in this design.

2.6. Classification and Performance Assessment

In order to detect the tremor episodes from extracted features, we evaluated the performance of different machine learning models and performed a hyperparameter tuning of classifiers in a patient-specific manner to determine the optimal settings. These models include the commonly used classification algorithms such as logistic regression (LR), support vector machines based on linear or RBF kernels (SVM-L, SVM-R), linear discriminant analysis (LDA), multilayer perceptron (MLP), K-nearest neighbors (KNN), and more recent models such as extreme gradient-boosted trees (XGB) and random forest (RF). The decision tree ensembles (e.g., gradient boosting and random forest) have been among the winning classifiers in ML challenges in recent years, performing remarkably well on small training datasets. We further examined the performance of ML algorithms that do not rely on handcrafted features or domain knowledge, such as convolutional neural network (CNN). We used a compact CNN previously employed for EEG classification. The CNN model was implemented using the AlexNet architecture of TensorFlow, with three convolutional layers, three average pooling layers, and a softmax output layer. During model training, a 32-samples input batch was fed to the CNN in each iteration and the weights were updated by backpropagation. Multiple iterations were conducted until a stable cross-validation score was obtained.

Here, all the features described in Table III were used for classification. We used a block-wise approach to partition the LFP recordings into training and test sets and to minimize the risk of data leakage. Each recording was first divided into twenty blocks of equal size. A five-fold cross-validation (CV) was subsequently applied, i.e., in each round, 80% of the LFP blocks were used to train the model and the rest to validate the performance. The results of five rounds were then averaged to assess the overall predictive performance. Given the unbalanced distribution of tremor/non-tremor episodes in our dataset, we measured the performance of classifiers by F1 score, sensitivity, and specificity, rather than accuracy. The F1 score is defined as $$2 \cdot \frac{\text{Sensitivity} \times \text{Precision}}{\text{Sensitivity} + \text{Precision}},$$

indicating the harmonic mean of the sensitivity and precision. It ranges from 0 to 1 with higher values representing better performance (precision is the fraction of true positive detections to the total positive detections returned by the classifier).

2.7. Examined Feature

Following model selection, we evaluated the predictive performance of features for the top performing classifier (XGB, as later shown in Section 3.2) to assess the relative feature importance and potentially reduce the feature computation overhead. Here, a sequential feature selection (SFS) method was utilized. The algorithm first evaluates all single-feature subsets to find the most predictive biomarker. In each subsequent iteration, the performance of the previous subset combined with a new element from the remaining feature set is investigated to find the next "best feature", using F1 score measured by 5-fold CV. The algorithm continues to successively add new features and update the subset until all features are analyzed.

2.8. Detection Latency

Figure 17:
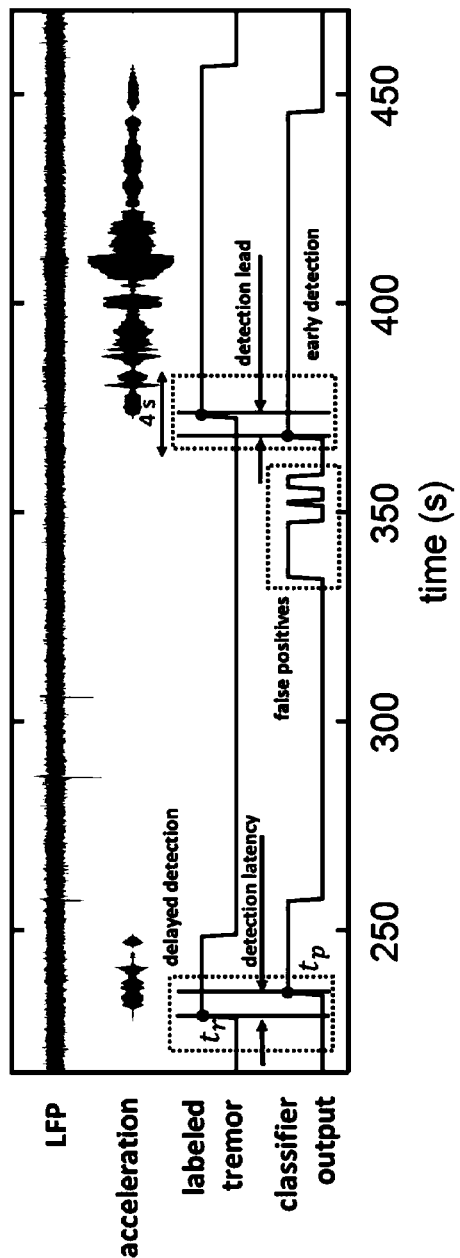
FIG. 17 shows latency calculation in an example patient. The time difference between the onset of classifier output ($t_p$) and the onset of labeled tremor ($t_r$) is defined as detection latency.

In addition to detection rate, the timing of stimulation in adaptive DBS is also critical for modulation to be effective, and to be used as a reliable alternative for conventional DBS. In this patent document, the latency in tremor detection is measured with reference to the labeled tremor onset, showing how early ahead (or late) a detection is raised by the model. To measure the latency of classifiers, we define $t_r$ as the onset of tremor based on the labeled acceleration with the following conditions: (1) the state changes from non-tremor to tremor at $t_r$; (2) the next consecutive state starting at $t_r+w/2$ is also labeled as tremor, where w represents the window size and w/2 is the overlap. Similarly, we define $t_p$ as the predicted onset of tremor based on the output of classifier, with the following two criteria: (1) the predicted state changes from non-tremor to tremor at $t_r$; (2) the subsequent state starting at $t_p+w/2$ is predicted as tremor. Then, the latency is calculated by $t_p-t_r$ based on the nearest prediction within a range of 4 s around $t_r$, as shown in FIG. 17.

In the current dataset, some patients exhibit continuous tremor-like activity, lacking a clear transition from the non-tremor to tremor state. For latency analysis, we chose those patients who had at least one clear tremor onset ($t_r$) and one correctly detected tremor onset ($t_p$) as described above. With this condition, 7 patients (9 recordings) were included in our latency analysis. The average detection latency of individual patients is used to quantify the overall latency.

2.9. Statistical Analysis

We used a one-way repeated measures ANOVA to compare the correlation coefficient among biomarkers (15 levels corresponding to the features in Table III), to compare the F1 score for different channel configurations (3 levels: monopolar, bipolar between adjacent channels [0-1,1-2,2-3], and bipolar [0-2,1-3]), and to compare the F1 score for different window sizes and overlapping (6 levels: 2 s without overlap, 2 s with half overlap, 1 s without overlap, 1 s with half overlap, 0.5 s without overlap, and 0.5 s with half overlap). In addition, a two-way ANOVA with repeated measures was applied to study the impact of Kalman filtering (2 levels: with and without Kalman filter) and classifiers (8 levels: LDA, LR, KNN, SVM-L, SVM-R, MLP, RF, and XGB) on the classification performance. We used the IBM SPSS Statistics Version 22 for the statistical analyses presented here. Mauchly's test for sphericity was performed for repeated measures and in cases where the sphericity assumption was violated, the results were Greenhouse-Geisser corrected. Multiple comparisons with Bonferroni correction were used for post-hoc comparison when the main effect was significant (p<0.05).

VIII.3. Results 3.1. STNr LFP Biomarkers for Quantifying Resting Tremor

Figure 18:
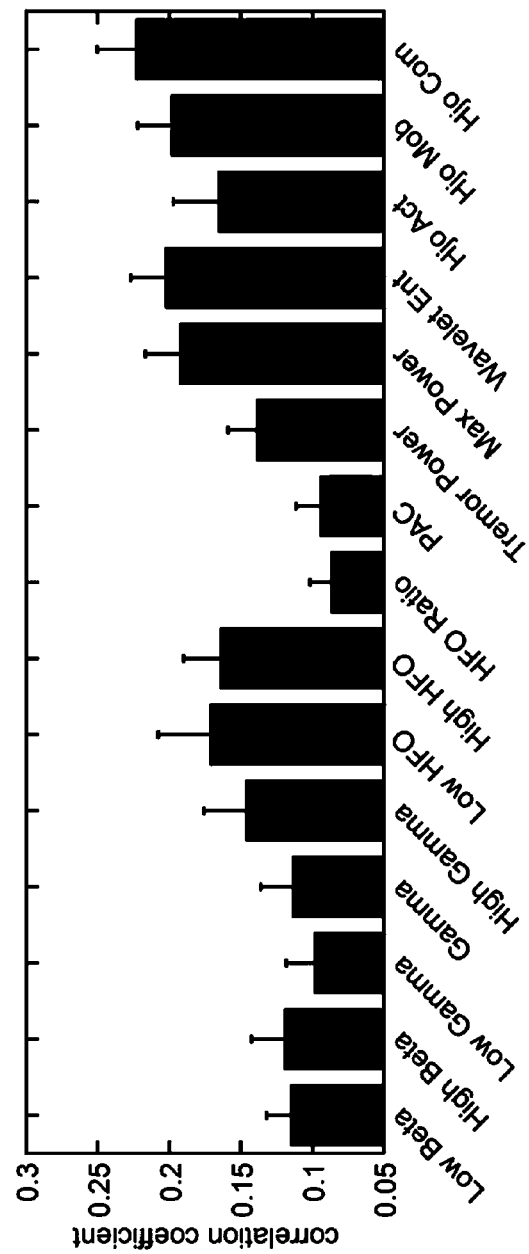
FIG. 18 shows Correlation coefficients of features with tremor, where for each feature, the channel with the maximum correlation coefficient has been used and the error bars indicate the standard error.

FIG. 18 depicts the correlation coefficient of each feature with tremor. The one-way ANOVA with repeated measures showed a significant difference in the examined electrophysiological biomarkers (Greenhouse-Geisser corrected F (5.0,75.0)=6.4, p<0.0001), and the Hjorth complexity exhibited a higher correlation with tremor compared to other features. No significant difference was observed between low beta vs. high beta (p=0.72), neither between low and high HFO (p=0.84), in our dataset.

3.2. Kalman Filtering to Enhance the Specificity

Figure 19:
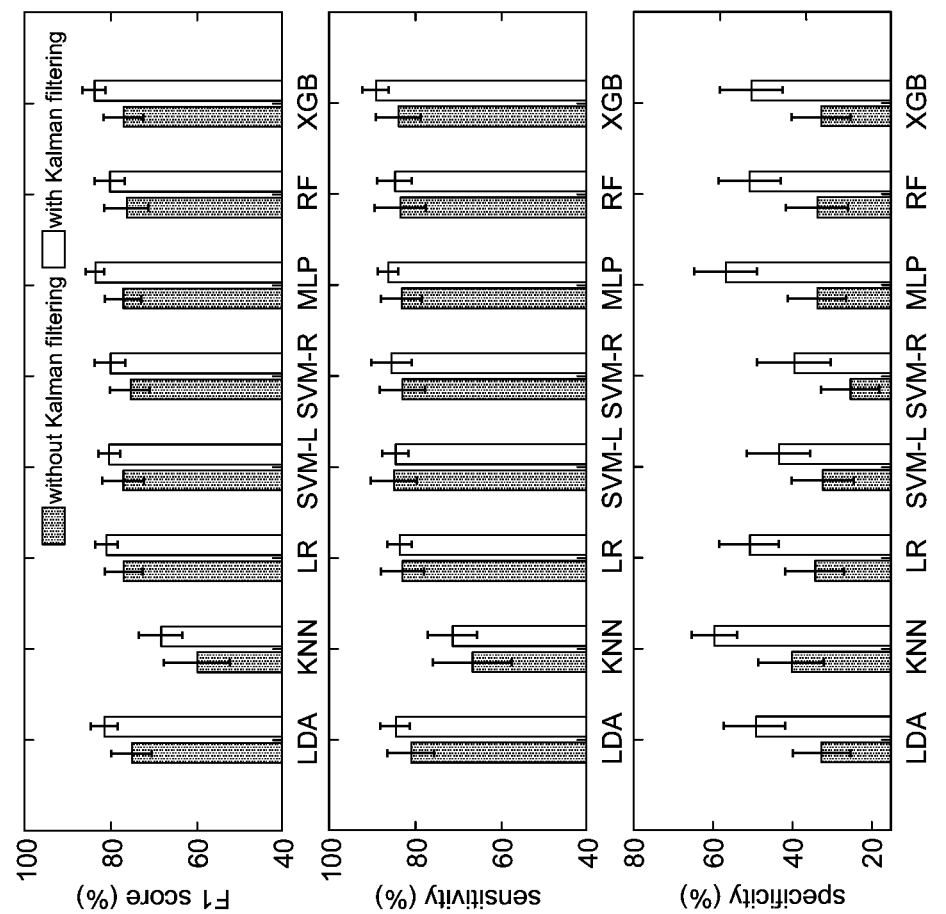
FIG. 19 shows performance of different classifiers in tremor detection, with and without Kalman filtering. The performance is measured by F1 score, sensitivity, and specificity, where the error bar indicates the standard error.
Figure 20:
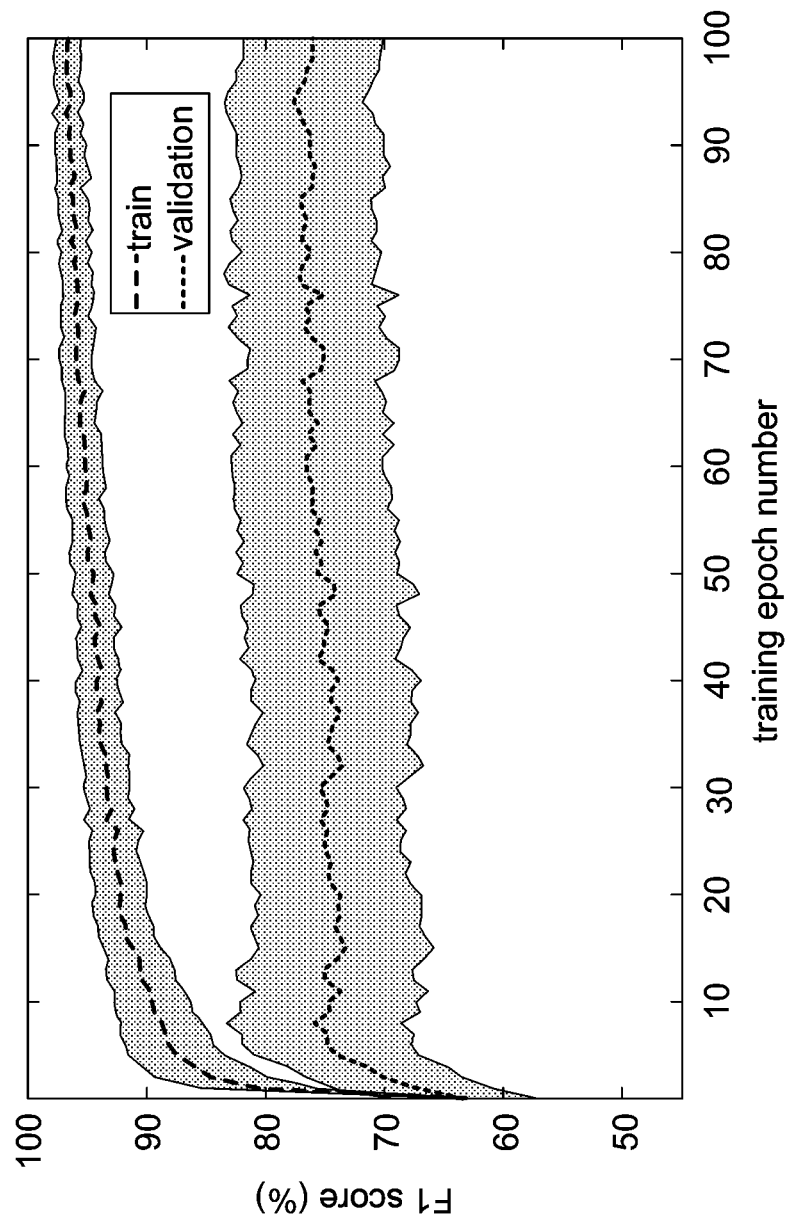
FIG. 20 shows a performance of compact CNN on the training and validation sets across consecutive training epochs. The gray area indicates the standard error across patients.

FIG. 19 compares the classification performance of different ML models using the feature set in Table III, and the effect of Kalman filtering. For F1 score, a two-way repeated measures ANOVA showed a marginal effect of Kalman filter (F (1,15)=4.19, p=0.058) and a significant effect of classifiers (Greenhouse-Geisser corrected F (1.3,18.8)=5.37, p=0.026) with no interaction. For the sensitivity measure, the classifiers showed a significant main effect (Greenhouse-Geisser corrected F (1.4,20.4)=5.02, p=0.027), while all classifiers except KNN showed comparable performance. For the specificity measure, the two-way repeated measures ANOVA showed a significant main effect of Kalman filter (F (1,15)=14.62, p=0.002) and of ML models (Greenhouse-Geisser corrected F (2.7,40.8)=3.83, p=0.019) with no interaction. Moreover, the Kalman filtering resulted in a 17.0% higher specificity compared to the cases without Kalman filtering. The XGB classifier obtained the highest F1 score (84.0%±10.8%) and sensitivity (89.2%±12.0%), while KNN achieved the highest specificity (59.6%±23.1%) on this dataset. The tremor detection performance for each recording based on the XGB model is shown in Table IV. The CNN classifier obtained an F1 score of 77.1%±18.3%, sensitivity of 81.7%±20.1%, and specificity of 37.8%±30.1%. FIG. 20 depicts the performance of CNN while increasing the number of training epochs to the network. On average, the performance reached its maximum value after 10 training epochs.

TABLE IV

Tremor detection performance for each recording using the XGB classifier, where K and N denote the performance with and without Kalman filtering.

| Recording index | F1 Score (%) | | Sensitivity (%) | | Specificity (%) | |
| --- | --- | --- | --- | --- | --- | --- |
| | N | K | N | K | N | K |
| 1 | 88.7 | 84.9 | 98.5 | 88.6 | 5.6 | 28.5 |
| 2 | 68.9 | 78.1 | 70.0 | 80.8 | 69.4 | 74.9 |
| 3 | 39.6 | 69.0 | 43.7 | 70.9 | 72.1 | 82.3 |
| 4 | 96.3 | 98.6 | 99.6 | 100.0 | 32.5 | 82.5 |
| 5 | 36.8 | 63.0 | 33.7 | 63.7 | 70.4 | 79.7 |
| 6 | 81.6 | 84.0 | 94.8 | 93.0 | 9.5 | 34.6 |
| 7 | 70.8 | 76.2 | 73.3 | 80.4 | 75.4 | 76.2 |
| 8 | 92.5 | 92.4 | 100.0 | 99.9 | 0.0 | 0.5 |
| 9 | 90.9 | 98.0 | 98.8 | 98.8 | 4.0 | 66.9 |
| 10 | 70.4 | 71.4 | 76.7 | 77.5 | 52.3 | 65.3 |
| 11 | 81.5 | 91.0 | 88.0 | 96.0 | 30.3 | 69.7 |
| 12 | 65.4 | 75.8 | 73.4 | 80.6 | 64.4 | 77.1 |
| 13 | 95.1 | 95.1 | 100.0 | 100.0 | 0.0 | 0.0 |
| 14 | 92.3 | 92.3 | 100.0 | 100.0 | 0.0 | 0.0 |
| 15 | 73.4 | 84.0 | 95.5 | 100.0 | 11.4 | 43.6 |
| 16 | 89.1 | 89.7 | 95.7 | 97.2 | 26.5 | 24.5 |
| Mean | 77.1 ± 18.3 | 84.0 ± 10.8 | 83.9 ± 20.8 | 89.2 ± 12.0 | 32.7 ± 29.8 | 50.4 ± 31.4 |

Figure 21A:
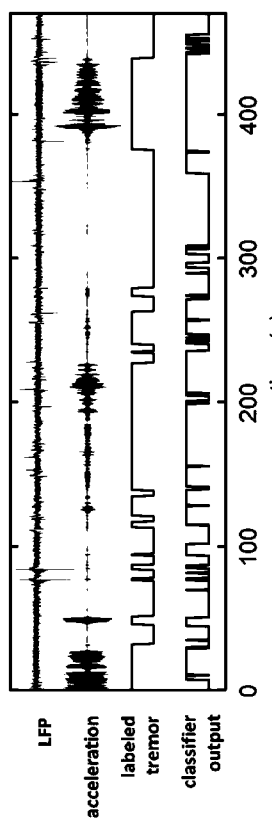
FIGS. 21A-21C show examples of tremor detection on three sample LFP recordings, there the bipolar LFP, measured acceleration, labeled tremor, and classifier output are shown, and where the binary output of XGB classifier that is built upon LFP features successfully tracks the episodes of tremor.
Figure 21B:
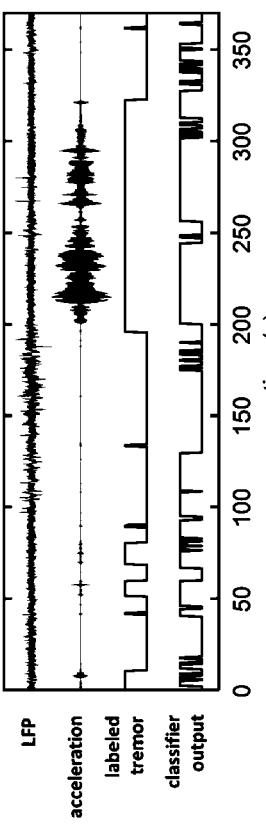
Figure 21C:
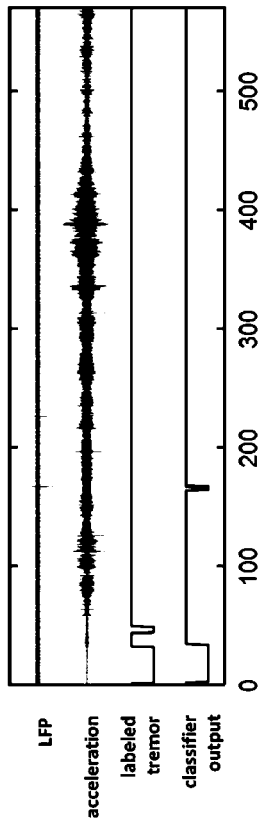

Using Kalman filter and XGB, the simulated classification results for three representative LFP recordings are illustrated in FIGS. 21A-21C, showing a reasonable detection of tremor state. Specifically, for patients with prolonged episodes of weak or strong tremor (FIG. 21A), the proposed method can reliably detect the presence of tremor in the majority of cases. Our approach was also effective on recordings with a single prolonged tremor (FIG. 21B) while raising a number of false positives for small motions during the non-tremor state. Finally, for recordings with a high tremor prevalence (FIG. 21C), the algorithm could reliably detect the tremor episode.

3.3. Other Design Parameters

In addition to the type of classifier and features, the other parameters that may affect the classification performance include the window size, sampling rate, and channel configuration, which are discussed in the following. We further investigated the optimal number of features that led to the highest classification performance. For the following analysis, we use XGB combined with Kalman filter, as it showed a superior performance in tremor detection.

3.3.1. Window Size and Overlapping

The classification performance and latency for different window lengths and overlaps are depicted in FIG. 22A-22D. Here, we observed a nearly similar performance in terms of F1 score (Greenhouse-Geisser corrected F (2.7,39.7)=0.43, p=0.71). As expected, shorter windows and the use of overlapping improved the detection latency. Overall, the 1-second window with half overlapping achieved a reasonable trade-off between detection performance and latency.

3.3.2. Bipolar and Monopolar Channel Configurations

Figure 22A:
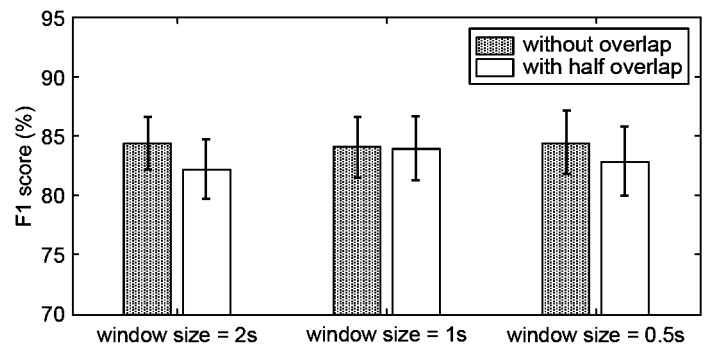
FIGS. 22A-22E show performance for different window sizes and overlaps, where
Figure 22B:
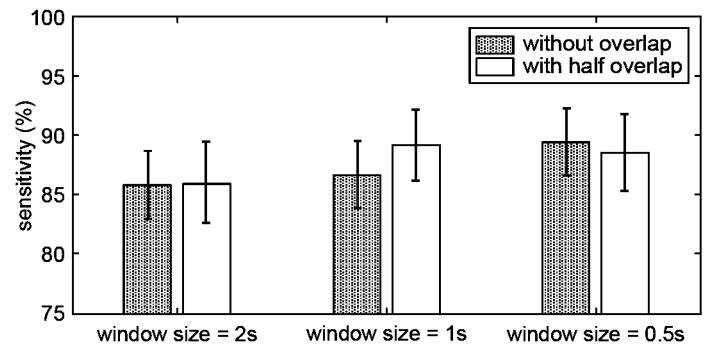
Figure 22C:
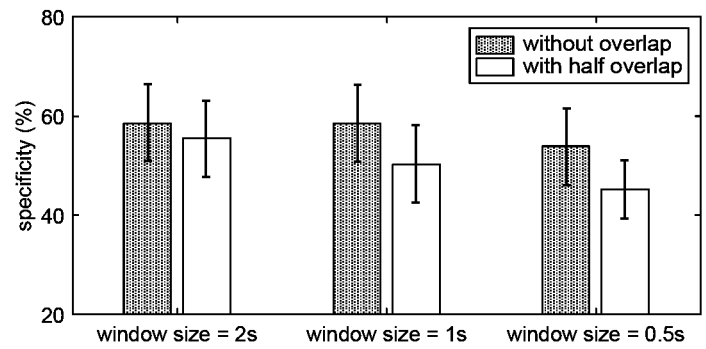
Figure 22D:
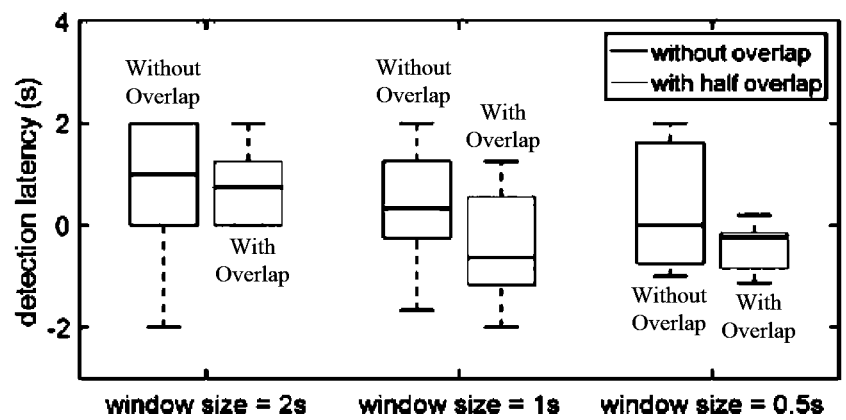
Figure 22E:
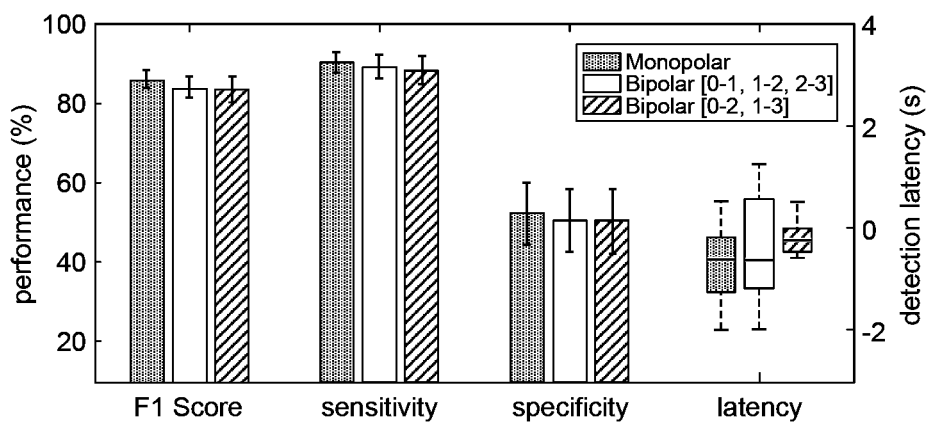

The performance and detection latency for the monopolar and two bipolar configurations using a 1-second window and half overlapping are shown in FIG. 22E. The one-way ANOVA with repeated measures showed no significant difference in terms of F1 score (Greenhouse-Geisser corrected F (1.5,22.3)=1.74, p=0.20) among the three configurations. Moreover, by only using the 0-2 or 1-3 bipolar channel for classification, no significant deterioration in performance was observed. The monopolar configuration led to a lower detection latency, but it was not significant. Considering that in practice, a bipolar configuration would limit the impact of stimulation artifact by canceling it as a common-mode input, we opted to use the bipolar method in this patent document.

3.3.3. Sampling Rate

Although we used a high sampling rate (2048 Hz) to capture the high-frequency content in LFPs, this may increase the hardware complexity and power dissipation of the processing circuitry. To study the effect of sampling rate, we reduced the date rate to 512 Hz and excluded the HFO-based features (low HFO, high HFO, HFO ratio, PAC) from our analysis. We observed that the performance slightly degraded at lower sampling rates (F1 score of 84.0%±11.2%, sensitivity of 88.6%±13.3%, and specificity of 49.5%±35.0%).

3.3.4. Optimal Number of Biomarkers

Figure 23:
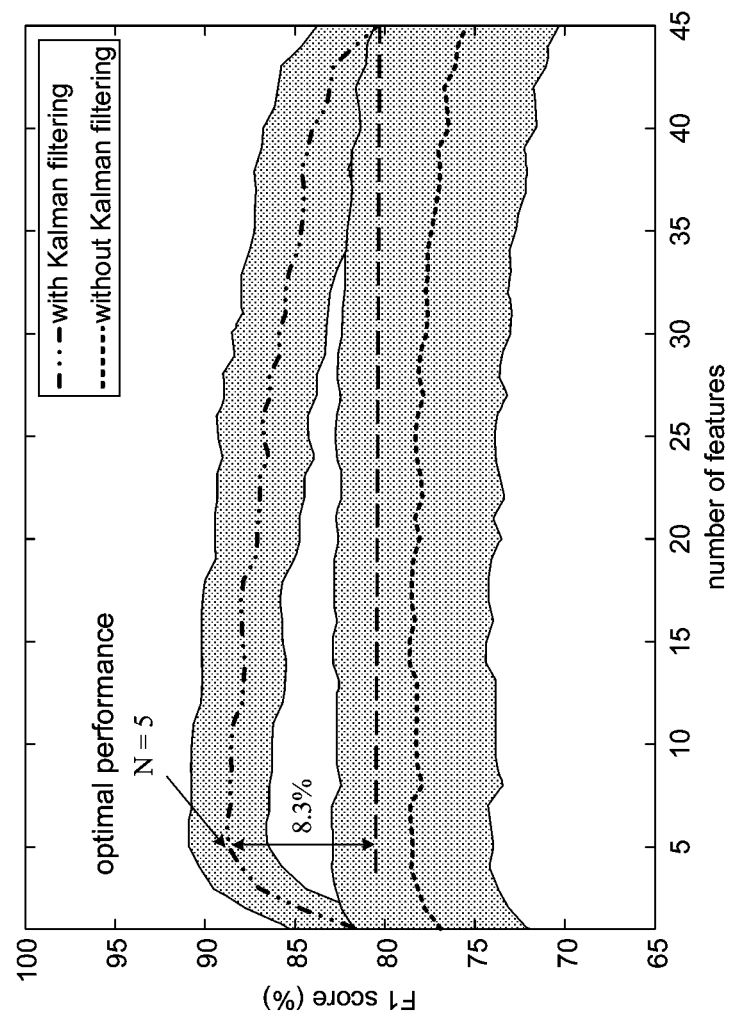
FIG. 23 shows a grand-averaged classification performance with respect to number of features using the sequential feature selection method, where the arrow shows the setting that leads to the highest performance on average, using the same XGB model for all patients, and where the gray area indicates the standard error across patients.
Figure 24:
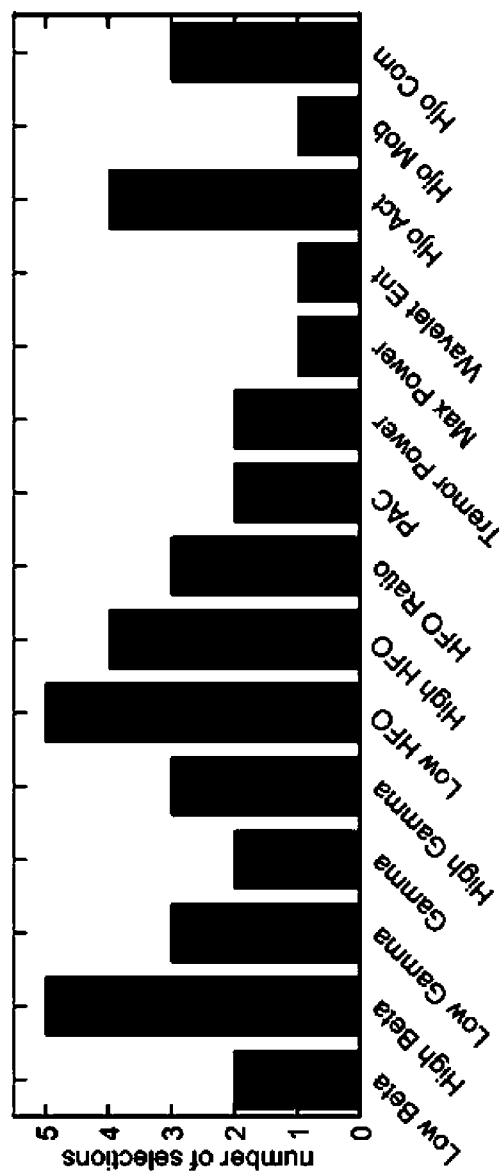
FIG. 24 shows a distribution of the number of times a feature is selected across patients, where a subject-specific number of features is used for each patient (min 1, max 5), and where features are selected from more than one channel in a patient are counted as one.

In order to reduce the feature count and assess the importance of different biomarkers in the overall classification performance, the number of input features to the XGB model was successively increased based on the SFS method, as depicted in FIG. 23. We observed that performance can be further improved by optimally selecting as low as only five features or less, from each patient. For equal number of features, the F1 score with Kalman filtering was generally higher than the case without Kalman filter. This figure shows that the average F1 score for the XGB model can reach 88.7%±8.5%, which is 8.3% higher compared to using all 45 features. The detection latency for this optimal setting was −0.52±1.14 s (i.e., detection lead of 0.52±1.14 s). The most discriminative features using the SFS method and XGB classifier are outlined in Table V for each LFP recording. The stopping criterion is when adding a new feature improves the F1 score by less than 1%, with a maximum of 5 features selected in each case. With this process, the distribution of selected features for the patients in our dataset is shown in FIG. 24, in which the high beta, low HFO, high HFO, and Hjorth parameters are among the most commonly selected features. While the correlation analysis did not show any significant difference between the low and high beta features, the latter is more frequently selected as an important feature for tremor detection in this study.

TABLE V

The top performing features with XGB model.

| Recording index | Most discriminative features |
|---|---|
| 1 | High Beta |
| 2 | High Gamma, Low Beta, Hjo Com |
| 3 | High Beta, Gamma, Hjo Act, Low Beta |
| 4 | High Gamma |
| 5 | Tremor Power, High Beta, HFO Ratio, Max Power, Wavelet Ent |
| 6 | Hjo Com, HFO Ratio, High HFO |
| 7 | HFO Ratio, Wavelet Ent, Low Gamma, Hjo Com, High HFO |
| 8 | Hjo Mob |
| 9 | Low Beta |
| 10 | Gamma, High HFO, HFO Ratio |
| 11 | High Gamma, HFO Ratio, Hjo Com |
| 12 | High HFO, PAC, Low HFO, Tremor Power |
| 13 | Hjo Act |
| 14 | High Gamma, Gamma |
| 15 | Gamma, Low Beta, High HFO |
| 16 | Gamma |

Hjo = Hjorth,
Act = Activity,
Mob = Mobility,
Com = Complexity.

VIII.4. Discussion

In this patent document, we systematically analyzed the neurophysiological biomarkers in the STNr LFP in a machine learning framework, with the goal of accurately detecting resting tremor in PD. To the best of our knowledge, this is the first use of Kalman filtering as a post feature processing approach to enhance tremor detection performance. The Kalman filtering had a significant impact on specificity for all the studied classifiers. The enhancement of specificity is critical to limit the number of false positive detections and thereby to minimize DBS power consumption and side effects.

4.1. The Choice of Feedback Signal

To detect the onset of tremor from local field potentials, we need to properly identify and label tremor episodes for model training. Here, we placed a peripheral accelerometer sensor on patients' hands to measure their tremor intensity. Then, we adopted a thresholding method to separate the tremor and non-tremor periods, similar to the methods used elsewhere. As an alternative feedback signal, the tremor severity measured by peripheral sensors or surface EMG could be used to control DBS. For example, the peripheral measurements of the tremulous limb have been utilized to guide the stimulation and suppress tremor. However, this approach may impose an additional requirement on patient compliance, as well as security concerns for wireless telemetry between the implant and the wearable sensor. To implement adaptive DBS, the combination of informative biomarkers based on neuronal activity (e.g., STN LFPs or ECoG in motor cortex) may be preferred as they directly reflect brain activities that may underlie symptoms. For example, the cortical narrow gamma (60-90 Hz) oscillations pertaining to dyskinesia have been used to control DBS, while reducing energy consumption by 38% to 45% and maintaining therapeutic efficacy. Ideally, a combination of both depth and cortical biomarkers may provide a more precise and/or reliable approach for the closed-loop control of DBS and enable the targeting of multiple PD symptoms. For instance, cortical biomarkers could be used in place of the low-amplitude STN HFOs that are difficult to detect in the presence of stimulation artifact, while these sensitive STN biomarkers could accurately detect the onset of tremor (as shown in this patent document) and activate DBS in the first place. The advantage of our proposed framework is that a handful of most relevant biomarkers can be selected in a patient-specific manner and combined with powerful classification algorithms, without the need to prioritize and threshold a single depth or cortical biomarker that could, in turn, sacrifice the efficacy or energy efficiency of the adaptive DBS. In addition to detection performance, the physical and practical constraints of the system should be carefully considered when choosing the feedback signal for aDBS, such as the need for additional implants, any required changes in the surgical procedure, and patient comfort and compliance. Our current study is based on LFPs in STNr, with the advantage that no additional implant is needed and no change in the standard surgical procedure for DBS. Moreover, the multiple biomarkers extracted from the LFP may allow for the better personalization and adaptability of therapy to account for inter-subject variability.

4.2. Features, Classifiers, and Kalman Filter

Multiple LFP biomarkers and a feedforward neural network were previously used for resting tremor detection, achieving a classification accuracy of over 86% in 4 out of 8 patients. However, due to the unbalanced duration of tremor/non-tremor episodes in most patients, the classification accuracy may not be appropriate for quantifying the performance. In the current study, we further demonstrated the possibility of successful tremor detection on 12 patients with diverse tremor characteristics and durations, using relevant biomarkers in the STNr LFP, state-of-the-art ML models, and Kalman filtering. If we instead apply a median threshold to beta power only, similar to most prior studies, the F1 score, sensitivity and specificity dropped to 49.6%±9.9%, 44.7%±9.0% and 47.3%±24.04%, respectively. Moreover, using the HMM model on our feature set, we obtained an F1 score of 56.3%±15.5%, sensitivity of 48.2%±16.4% and specificity of 55.5%±23.6%, while Kalman filter is not effective in this case. The CNN model with embedded feature learning led to an F1 score of 77.1%±18.3%, sensitivity of 81.7%±20.1%, and specificity of 37.8%±30.1%. Therefore, our feature-engineered approach showed a superior performance in the current dataset. In general, while deep learning models obtain an outstanding performance on large and unstructured datasets such as provided by imaging, they may not be optimal for problems with limited training data. In this patent document, we used the Hjorth parameters for tremor analysis in PD. Interestingly, the Hjorth complexity, which is a measure of the change in frequency, showed a higher correlation with tremor compared to other features. The underlying neurophysiological mechanism that contributes to the correlation of Hjorth complexity with tremor may be worth further study. The use of Kalman filter in feature space was motivated by prior studies on epileptic seizure detection and emotion classification from EEG. In this patent document, the Kalman filter improved the tremor detection performance of different classifiers, by reducing the noisy fluctuations of the features. Due to the inherent noise in the neural system and the corresponding LFP recordings, a second-order Kalman filter provided a suitable way to model this noisy activity, thereby successfully tracking the tremor state. The Kalman filter offers the potential benefit of enhancing the detection specificity without degrading the sensitivity of the classifier, thus improving the energy efficiency in aDBS. Furthermore, we tested the potential use of Kalman filter after classification, which proved to be less effective compared to filtering in feature space for tremor detection.

The classification results in FIGS. 21A-21C show that our algorithm performs well on typical patients that have sustained tremor periods. For patients with shorter tremor episodes, our algorithm raises a number of false positives. In this patent document, we used Kalman filtering to lower the number of false positives and achieved 17% improvement in specificity on average. The other potential approach to limit the false positive rate is to increase the number of successive detections required to define tremor, e.g., by defining tremor onset after three positive detections.

4.3. Channel Configuration

Considering that in a closed-loop approach, the DBS electrodes would be used for both sensing the neural activity and stimulation, this would unavoidably cause a strong stimulation artifact at the recording site. The bipolar configuration provides a way to reduce this effect, by partially canceling the common-mode artifact component. In this patent document, we compared the classification performance of monopolar and two bipolar configurations, and no significant difference was found in the absence of stimulation. Our analysis showed that a single bipolar combination (0-2 or 1-3) leads to a comparable performance, which could further reduce hardware complexity. To minimize the potential impact of stimulation artifact on the classifier performance, we also tested our algorithm by excluding the high-gamma feature (100-200 Hz), and the results showed no significant decline in performance. More advanced circuit techniques will be explored to suppress the artifact both at the input of amplifiers and digitally in the back-end, in order to enable a robust implementation of adaptive DBS.

4.4. Features

In the current approach for labeling the data, we visually identified a low-activity time period as baseline. Then, a threshold was empirically set by calculating the average and standard deviation for the baseline. However, we had to slightly adjust the threshold in some patients to avoid the abrupt transitions in labels due to noise or artifact in the acceleration signal. Alternatively, the accelerometer could be combined with other methods such as video recording and EMG sensing in order to more reliably define and label the tremor episodes for model training.

It has been previously shown that amplitude-responsive aDBS decreases the total energy delivered to the tissue by ~130 mW per side, while the energy dissipated by a single-channel power classifier is of the order of 10 mW. Through system-on-chip integration in modern CMOS technologies, power dissipation in the range of sub-microwatt per channel has recently been reported for epileptic seizure detection, and a very low energy of 41.2 nJ/class for computing 12 features with an XGB classifier. Moreover, while a high voltage compliance is required for stimulation, recording can be reliably done at a lower supply voltage. Considering that sensing, feature computation, and classification could be performed with low energy, aDBS could potentially save total battery usage, in addition to the saving in energy delivered to the tissue through stimulation (and thereby the reduction in side-effects). The actual computational overhead and energy consumption for the proposed algorithm needs to be investigated and compared with the potential saving in stimulation energy. An optimal sampling rate that enables a good trade-off between detection accuracy and energy should be further explored. Moreover, the performance in this study was evaluated offline, while an online evaluation of the proposed approach should be performed to further validate its efficacy in real-time and during closed-loop operation. The effect of stimulation artifact on the tremor detection circuitry should be studied in order to efficiently integrate this method into the DBS system.

Efficient integration of multiple biomarkers and advanced control algorithms could potentially improve the therapeutic efficacy of aDBS. Although aDBS has mostly been realized using external devices this is not exclusively the case. Medtronic's implantable research system, the Activa PC+S, has been used for neural recording and stimulation in essential tremor and PD, and for acute trials of aDBS in Parkinsons. The investigational Summit RC+S (Medtronic) embeds basic spectral analysis algorithms and an LDA classifier. The design of a low-power and miniaturized ASIC with integration of sensing, optimal biomarker extraction, advanced classification, and stimulation could enable high quality, low-noise recording and more effective intervention. Also, while the use of multiple biomarkers may account for inter-subject variability, more research is required to translate this approach into an effective personalized therapy.

Here, as a proof-of-concept, we demonstrated our approach in the form of a binary classifier that could activate an on-demand stimulator. However, it is also possible to use this framework in a truly adaptive manner, by predicting the tremor strength using a regressor or a multi-class machine learning method to adaptively control the stimulation amplitude. Finally, we limited our analyses to Parkinsonian rest tremor, and the confounding effects, if any, of voluntary movement remain to be investigated, as does the detection of Parkinsonian action or postural tremor.

VIII.5. Concluding Remarks

In this patent document, we disclosed a number of neurophysiological biomarkers in the LFP signal from the STNr, and various classification algorithms to detect resting tremor episodes in Parkinson's disease. By combining a powerful machine learning model with relevant patient-specific features in the LFP, and using Kalman filtering, we achieved an average F1 score of 88.7% and detection lead of 0.52 s. This patent document demonstrates the potential use of a more accurate ML-based approach for resting tremor detection and adaptive DBS control in Parkinson's disease.

Figure 13:
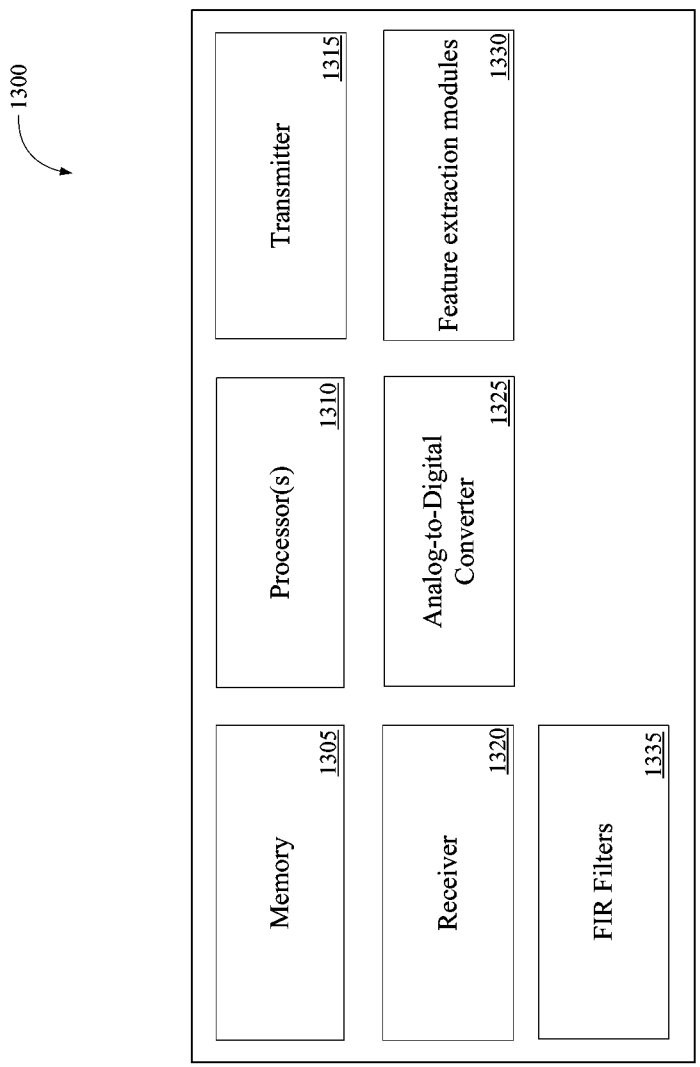
FIG. 13 shows an exemplary block diagram of a hardware platform that performs the operations described in this patent document.

FIG. 13 shows an exemplary block diagram of a hardware platform 1300 that performs the operations described in this patent document. The hardware platform 1300 includes at least one processor 1310 and a memory 1305 having instructions stored thereupon. The instructions upon execution by the processor 1310 configure the hardware platform 1300 to perform the operations described for the technology described in FIGS. 1 to 12 and 14 to 25 and in the various embodiments described in this patent document. The transmitter 1315 transmits or sends information or data to another device. For example, the transmitter 1315 may send a decision related information (e.g., a presence of a physiological condition) to another device (e.g., a computer or a mobile device) to inform a person of a determined decision. The transmitter 1315 may also send out the raw neural data to another device (e.g., computer) for offline training of the on-chip classifier (e.g., once to calibrate the hardware platform). The receiver 1320 receives information or data transmitted or sent by another device. For example, a receiver 1320 may receive trained model parameters from an external device (e.g., during calibration/training).

Figure 25:
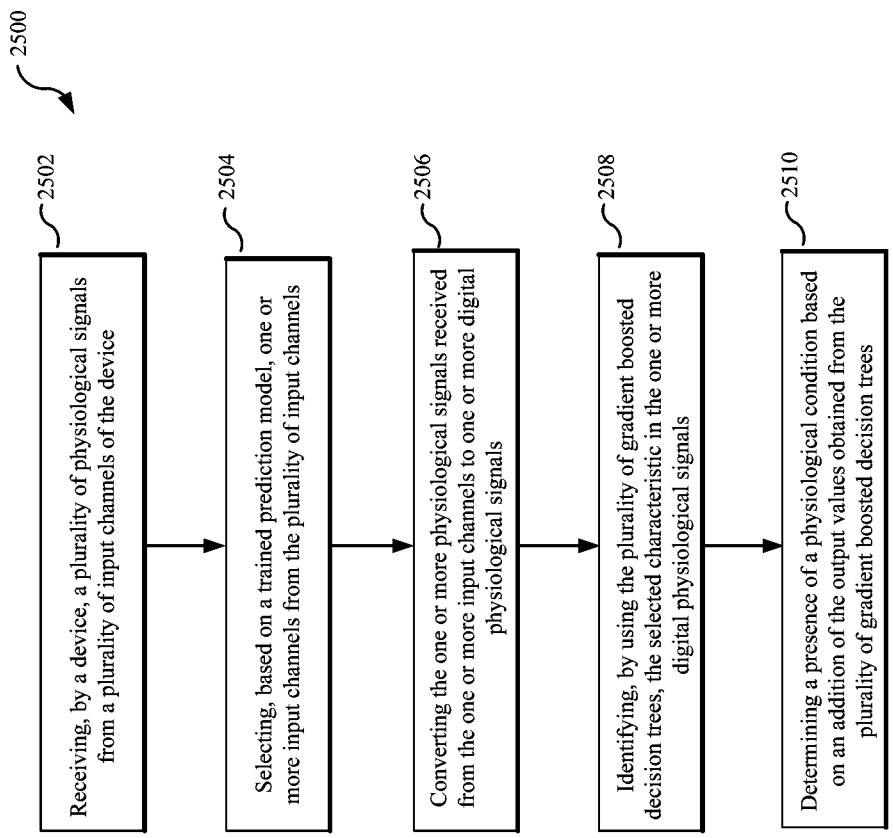
FIG. 25 shows an example flowchart of a method of detecting a biological condition.

FIG. 25 shows an example flowchart of a method of detecting a biological condition. Operation 2502 includes receiving, by a device, a plurality of physiological signals from a plurality of input channels of the device. Operation 2504 includes selecting, based on a trained prediction model, one or more input channels from the plurality of input channels, where the trained prediction model indicates the one or more input channels and configurations of a plurality of gradient boosted decision trees for identification of a selected characteristic of one or more physiological signals from the plurality of physiological signals. Operation 2506 includes converting the one or more physiological signals received from the one or more input channels to one or more digital physiological signals. Operation 2508 includes identifying, by using the plurality of gradient boosted decision trees, the selected characteristic in the one or more digital physiological signals, where the identifying the selected characteristic includes providing output values by the plurality of gradient boosted decision trees. The gradient boosted decision trees are associated with the feature extraction module or feature extraction engine (FEE) as described in this patent document. The selected characteristic may include any one or more features as described in Tables I and/or III in this patent document. Operation 2510 includes determining a presence of a physiological condition based on an addition of the output values obtained from the plurality of gradient boosted decision trees. As an example, the presence of the physiological condition may include detection of a seizure or detection of a Parkinsonian resting tremor as explained in this patent document.

In some embodiments, the plurality of gradient boosted decision trees operate in parallel, the identifying the characteristic is performed within an optimum time that is determined based on a plurality of times associated with the plurality of gradient boosted decision trees, and each of the plurality of times indicate an amount of time associated with obtaining an output value from an associated gradient boosted decision tree. In some embodiments, each gradient boosted decision tree is associated with a programmable finite impulse response (FIR) filter that filters or bypasses a digital physiological signal based on the selected characteristic. In some embodiments, the device includes a memory that stores the plurality of gradient boosted decision trees and coefficient values for the programmable FIR filter for each gradient boosted decision tree, and the coefficient values are based on the selected characteristics. The technical advantages of having FIR filters for each gradient boosted decision tree and the memory design are described in the sections above in this patent document.

In some embodiments, the programmable FIR filter includes a first stage that outputs a downsampled physiological signal that is obtained by downsampling the digital physiological signal, the programmable FIR filter includes a second stage that includes a tunable bandpass filter that filters the downsampled physiological signal, and bandwidth related parameters of the tunable bandpass filter are determined based on the selected characteristic. In some embodiments, any one or more of the first stage and the second stage are bypassed based on the selected characteristic. In some embodiments, the selecting the one or more input channels is performed using a multiplexer associated with each of the plurality of gradient boosted decision trees. In some embodiments, the selecting, the converting, the identifying, and the determining is performed for the one or more input channels that are selected without buffering data from the plurality of input channels other than the one or more input channels. In some embodiments, a number of the plurality of gradient boosted decision trees is up to eight, and each gradient boosted decision tree has a maximum pre-determined depth of four.

In some embodiments, a classification method comprises performing a classification algorithm using a number of gradient boosted decision trees, wherein each gradient boosted decision tree comprises: a single feature extraction engine (FEE) including a number of finite impulse response (FIR) filters that continuously process an input channel selected from a plurality of input channels, and a single comparator that receives a first output from the single FEE and generates a second output, wherein a single path from a root node to the leaf node is processed by each gradient boosted decision tree when performing the classification algorithm, and wherein each gradient boosted decision tree operates in parallel; and obtaining a decision by combining the second output from the single comparator from each of the number of gradient boosted decision trees.

In some embodiments, the single FEE in each gradient boosted decision tree uses a single FIR filter structure in a closed-loop architecture, and the single FIR filter is associated with filter coefficients that are multiplexed from a shared memory. In some embodiments, the number of gradient boosted decision trees is less than or equal to eight. In some embodiments, the classification algorithm is performed in a sensor in a biomedical device to detect epilepsy.

In some embodiments, a classification method comprises determining an optimum time to update a decision of a system; performing a classification algorithm using a number of gradient boosted decision trees in a neural network, wherein each gradient boosted decision tree operates in parallel; and obtaining a decision by combining an output from each of the number of gradient boosted decision trees, wherein the performing the classification algorithm and the obtaining the decision is completed periodically within an interval defined by the determined optimum time.

Some aspects of the techniques and functional operations described in this specification can be implemented in digital electronic circuitry, or in computer software, firmware, or hardware, including the structural means disclosed in this specification and structural equivalents thereof, or in combinations of them. Some aspects can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

Some aspects of the processes and logic flows described in this specification can be performed by one or more programmable processors executing one or more computer programs to perform functions by operating on input data and generating output. Aspects of the processes and logic flows may be performed by, and apparatus can be implemented as, special purpose logic circuitry, e.g., an FPGA (field programmable gate array) or an ASIC (application specific integrated circuit).

Processors suitable for the execution of a computer program may include, by way of example, both general and special purpose microprocessors, and any one or more processors of any kind of digital computer. A processor typically receives instructions and data from a read-only memory or a random access memory or both. A computer includes a processor for executing instructions and one or more memory devices for storing instructions and data. A computer also typically includes, or is operatively coupled to receive data from or transfer data to, or both, one or more mass storage devices for storing data, e.g., magnetic, magneto optical disks, or optical disks. Devices suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Only a few implementations and examples are described and other implementations, enhancements and variations can be made based on what is described and illustrated in this patent document.

What is claimed is:

1. A method of detecting a biological condition, comprising:
  receiving, by a multiplexer of an implantable sensor device, a plurality of physiological signals from a plurality of input channels of the device;
  selecting, based on a trained prediction model, one or more input channels from the plurality of input channels received by the multiplexer, wherein the trained prediction model indicates the one or more input channels and configurations of a plurality of gradient boosted decision trees for identification of a selected feature of one or more physiological signals from the plurality of physiological signals, wherein each of the trees has a plurality of nodes and each of the nodes is associated with a respective one of the channels in memory;

converting the one or more physiological signals received from the one or more input channels selected by the multiplexer to one or more digital physiological signals;

selecting coefficients for a programmable finite impulse response (FIR) filter of a feature extraction engine (FEE) for the selected one or more input channels from a memory based on a feature to be processed by the programmable FIR filter;

inputting the one or more digital physiological signals to the FEE, wherein the FIR filter extracts a feature from the one or more digital physiological signals, the FEE being connected to a comparator, the comparator receiving an input feature from the FEE and implementing one of the plurality of gradient boosted decision trees, wherein the comparator compares the input feature to a threshold value for a current node of the one of the plurality of gradient boosted decision trees and generates an output of the comparator for the current node;

determining for the current node, using the output of the comparator, whether a next node is a leaf node, and:
 if the next node is not a leaf node, returning to selecting of one or more input channels;
 if the next node is a leaf node, output a result value; and determining a presence of a physiological condition based on an addition of the result values obtained from the plurality of gradient boosted decision trees.

2. The method of claim 1,
wherein a plurality of gradient boosted decision trees operate in parallel,
wherein the generation of the output of the comparator is performed within an optimum time that is determined based on a plurality of times associated with the plurality of gradient boosted decision trees, and
wherein each of the plurality of times indicate an amount of time associated with obtaining a result value from an associated gradient boosted decision tree.

3. The method of claim 2,
wherein a number of the plurality of gradient boosted decision trees is up to eight, and
wherein each gradient boosted decision tree has a maximum pre-determined depth of four.

4. The method of claim 1,
wherein the programmable FIR filter includes a first stage that outputs a downsampled physiological signal that is obtained by downsampling the digital physiological signal,
wherein the programmable FIR filter includes a second stage that includes a tunable bandpass filter that filters the downsampled physiological signal, and
wherein bandwidth related parameters of the tunable bandpass filter are determined based on the selected feature.

5. The method of claim 4, wherein any one or more of the first stage and the second stage are bypassed based on the selected feature.

6. The method of claim 1, wherein the selecting, the converting, and the determining is performed for the one or more input channels that are selected without buffering data from the plurality of input channels other than the one or more input channels.

7. An implantable sensor device receiving a plurality of physiological signals from a plurality of input channels, comprising;
 a multiplexer receiving the plurality of physiological signals from the plurality of input channels;
 a classifier for identifying a selected feature of one or more physiological signals from the plurality of physiological signals received by the multiplexer based on a trained prediction model that indicates the one or more input channels and configurations of a plurality of gradient boosted decision trees, each decision tree of the plurality of gradient boosted decision trees comprising a single feature extraction engine (FEE) that integrates a programmable finite impulse response (FIR) filter for multi-band filtering and spectral feature extraction, a digital comparator, and a Tree Control Unit (TCU), the FEE being connected to the comparator receiving an input from the FEE;
 a memory configured to store the trained prediction model having coefficient values based on the selected features for the programmable FIR filter and feature thresholds for each gradient boosted decision tree;
 a processor configured to send control signals to each FEE based on the trained prediction model for a respective gradient boosted decision tree to:
  select an input channel from the plurality of input channels received by the multiplexer, the input channel associated with a node of the respective gradient boosted decision tree;
  select coefficients for the programmable FIR filter from the memory based on a feature to be processed by the programmable FIR filter for the selected input channel wherein the FIR filter extracts a feature from the physiological signals received by the input channel, the comparator receiving the input from the FEE and implementing one of the plurality of gradient boosted decision trees, wherein the comparator compares the input to a threshold value for a current node of the one of the plurality of gradient boosted decision trees and generates an output of the comparator for the current node;
  determine for the current node, using the output of the comparator whether a next node is a leaf node, and:
   if the next node is not a leaf node, return to of selecting an input channel from the plurality of input channels;
   if the next node is a leaf node, output a result value;
  determine a presence of a physiological condition based on an addition of the result values obtained from the plurality of gradient boosted decision trees.

8. The device of claim 7,
wherein the processor is configured to identify the feature within an optimum time that is determined based on a plurality of times associated with the plurality of gradient boosted decision trees, and
wherein each of the plurality of times indicate an amount of time associated with obtaining a result value from an associated gradient boosted decision tree.

9. The device of claim 7,
wherein the programmable FIR filter includes a first stage that is configured to output a downsampled physiological signal obtained by downsampling the digital physiological signal,
wherein the programmable FIR filter includes a second stage that includes a tunable bandpass filter that is configured to filter the downsampled physiological signal, and wherein bandwidth related parameters of the tunable bandpass filter are determined based on the selected characteristic.

10. The device of claim 9, wherein any one or more of the first stage and the second stage are bypassed based on the selected characteristic.

11. A non-transitory machine-readable medium having machine executable instructions stored thereon that, when executed by one or more processors, direct the one or more processors to perform a method comprising:
   receiving, by a multiplexer of an implantable sensor device, a plurality of physiological signals from a plurality of input channels of the device;
   selecting, based on a trained prediction model, one or more input channels from the plurality of input channels received by the multiplexer, wherein the trained prediction model indicates the one or more input channels and configurations of a plurality of gradient boosted decision trees for identification of a selected feature of one or more physiological signals from the plurality of physiological signals wherein each of the trees has a plurality of nodes and each of the nodes is associated with a respective one of the channels in memory;
   converting the one or more physiological signals received from the one or more input channels selected by the multiplexer to one or more digital physiological signals;
   selecting coefficients for a programmable finite impulse response (FIR) filter of a feature extraction engine (FEE) for the selected one or more input channels from a memory based on a feature to be processed by the programmable FIR filter;
   inputting the one or more digital physiological signals to the FEE, wherein the FIR filter extracts a feature from the one or more digital physiological signals, the FEE being connected to a comparator, the comparator receiving an input feature from the FEE and implementing one of the plurality of gradient boosted decision trees, wherein the comparator compares the input feature to a threshold value for a current node of the one of the plurality of gradient boosted decision trees and generates an output of the comparator for the current node;
   determining for the current node, using the output of the comparator, whether a next node is a leaf node, and:
      if the next node is not a leaf node, returning to selecting of one or more input channels;
      if the next node is a leaf node, output a result value; and
   determining a presence of a physiological condition based on an addition of the result values obtained from the plurality of gradient boosted decision trees.

12. The non-transitory machine-readable medium of claim 11,
   wherein a plurality of gradient boosted decision trees operate in parallel,
   wherein the generation of the output of the comparator is performed within an optimum time that is determined based on a plurality of times associated with the plurality of gradient boosted decision trees, and
   wherein each of the plurality of times indicate an amount of time associated with obtaining a result value from an associated gradient boosted decision tree.

13. The non-transitory machine-readable medium of claim 11,
   wherein the programmable FIR filter includes a first stage that outputs a downsampled physiological signal that is obtained by downsampling the digital physiological signal,
   wherein the programmable FIR filter includes a second stage that includes a tunable bandpass filter that filters the downsampled physiological signal, and
   wherein bandwidth related parameters of the tunable bandpass filter are determined based on the selected feature.

* * * * *

UNITED STATES PATENT AND TRADEMARK OFFICE
CERTIFICATE OF CORRECTION

| | | |
|---|---|---|
| PATENT NO. | : 11,682,492 B2 | Page 1 of 1 |
| APPLICATION NO. | : 16/946151 | |
| DATED | : June 20, 2023 | |
| INVENTOR(S) | : Mahsa Shoaran et al. | |

It is certified that error appears in the above-identified patent and that said Letters Patent is hereby corrected as shown below:

On the Title Page

Item (72), Inventors:
"Benyamin Haghi, Ithaca, NY (US)" should read -- Beyamin Haghi, Pasadena, CA (US) --;
"Masoud Farivar, Ithaca, NY (US)" should read -- Masoud Farivar, Vaud (CH) --;
"Azita Emami, Ithaca, NY (US)", should read -- Azita Emami, Pasadena, CA (US) --.

Signed and Sealed this
Third Day of October, 2023

Katherine Kelly Vidal
*Director of the United States Patent and Trademark Office*